(12) United States Patent
Janssens et al.

(10) Patent No.: US 7,476,662 B2
(45) Date of Patent: Jan. 13, 2009

(54) SUBSTITUTED TETRACYCLIC IMIDAZOLE DERIVATIVES, PROCESSES FOR THEIR PREPARATION, PHARMACEUTICAL COMPOSITIONS COMPRISING THEM AND THEIR USE AS A MEDICINE

(75) Inventors: Frans Eduard Janssens, Bonheiden (BE); Joseph Elisabeth Leenaerts, Rijkevorsel (BE); Koenraad Arthur Van Rossem, Vosselaar (BE); Manuel Jesús Alcázar-Vaca, Toledo (ES); Pedro Martínez-Jiménez, Madrid (ES); José Manuel Bartolomé-Nebreda, Toledo (ES); Antonio Gómez-Sánchez, Toledo (ES); Francisco Javier Fernández-Gadea, Toledo (ES); Jos Van Reempts, Geel (BE)

(73) Assignee: Janssen Pharmaceutica N.V., Beerce (BE)

( * ) Notice: Subject to any disclaimer, the term of this patent is extended or adjusted under 35 U.S.C. 154(b) by 414 days.

(21) Appl. No.: 10/479,839

(22) PCT Filed: Jun. 11, 2002

(86) PCT No.: PCT/EP02/06576

§ 371 (c)(1),
(2), (4) Date: Dec. 5, 2003

(87) PCT Pub. No.: WO02/100862

PCT Pub. Date: Dec. 19, 2002

(65) Prior Publication Data

US 2004/0167138 A1    Aug. 26, 2004

(30) Foreign Application Priority Data

Jun. 12, 2001    (EP) ................................ 01202260

(51) Int. Cl.
*A61K 31/00*    (2006.01)
*A61P 43/00*    (2006.01)
*C07D 487/04*    (2006.01)
*C07D 519/00*    (2006.01)
*C07D 495/04*    (2006.01)
*C07D 487/14*    (2006.01)

(52) U.S. Cl. ................... 514/214.02; 540/578; 540/579
(58) Field of Classification Search ............ 514/214.02; 540/578, 579
See application file for complete search history.

(56) References Cited

FOREIGN PATENT DOCUMENTS

| WO | WO 88/05306 A1 | 7/1988 |
|---|---|---|
| WO | WO 92/06981 A1 | 4/1992 |
| WO | WO 92/22551 A1 | 12/1992 |
| WO | WO 92/22553 A1 | 12/1992 |
| WO | WO 94/13671 A1 | 6/1994 |
| WO | WO 94/13680 A1 | 6/1994 |
| WO | WO 94/13681 A1 | 6/1994 |
| WO | WO 95/02600 A1 | 1/1995 |
| WO | WO 97/24356 A1 | 7/1997 |
| WO | WO 97/34897 A1 | 9/1997 |
| WO | WO 99/13871 A2 | 3/1999 |

OTHER PUBLICATIONS

Chatelain P., et al., Cardiac ischaemia: possibilities for future drug therapy, European Journal of Mecidinal Chemistr, Editions Scientifique Elsevier, Paris, FR,. vol. 32, No. 9, Sep. 1997, pp. 687-707.
Stella, V.J. et al., "Prodrugs", Drug Delivery Systems, 1980, pp. 112-176.
Stella, V.J. et al., "Drugs", 1985, 29, pp. 455-473.
Engelborghs, K. et al., "Temporal changes in intracranial pressure in a modified experimental model of closed head injury", J. Neurosurg. 89:796-806, 1998.
Van Rossem, K. et al., "Brain oxygenation after experimental closed head injury", Adv. Exp. Med. Biol. 471: 209-215, 1999.
Engelborghs, K. et al., "Impaired autoregulation of cerebral blood flow in an experimental model of traumatic brain injury", J. Neurotrauma, 17(8): 667-677, 2000.
"Neuroprotection in CNS Disorders: Commercial Opportunities" A Jain PharmaBiotech Report, 2000, pp. 63-71.
International Search Report dated Dec. 17, 2002 for PCT/EP02/06576.

*Primary Examiner*—Brenda L Coleman

(57) ABSTRACT

The invention concerns novel substituted tetracyclic imidazole derivatives useful for the treatment of elevated intracranial pressure (ICP) and/or secondary ischaemia, in particular caused by brain injury, more in particular caused by traumatic (TBI) and non-traumatic brain injury, processes for their preparation, pharmaceutical compositions comprising them and their use as a medicine. The novel compounds comprise compounds according to the general Formula (I), the pharmaceutically acceptable acid or base addition salts thereof, the stereochemically isomeric forms thereof and the N-oxide form thereof. In particular, the preferred compound is 3-[2-[4-(11,12-dihydro-6H-benzimidazo[2,1-b][3]benzazepin-6-yl)-2-(phenyl-1-methyl)-1-piperidinyl]ethyl]-2,10-dimethyl pyrimido[1,2-α]benzimidazol-4(10H)-one, the pharmaceutically acceptable acid or base addition salts thereof, the stereochemically isomeric forms thereof and the N-oxide form thereof.

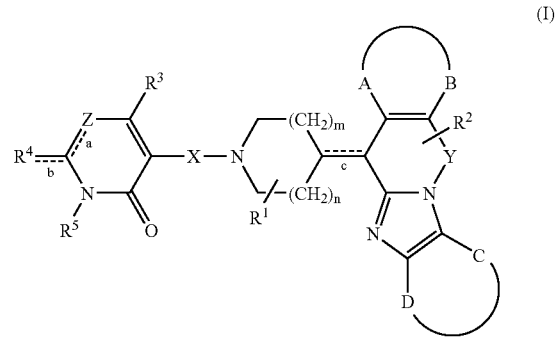

19 Claims, 3 Drawing Sheets

Figures

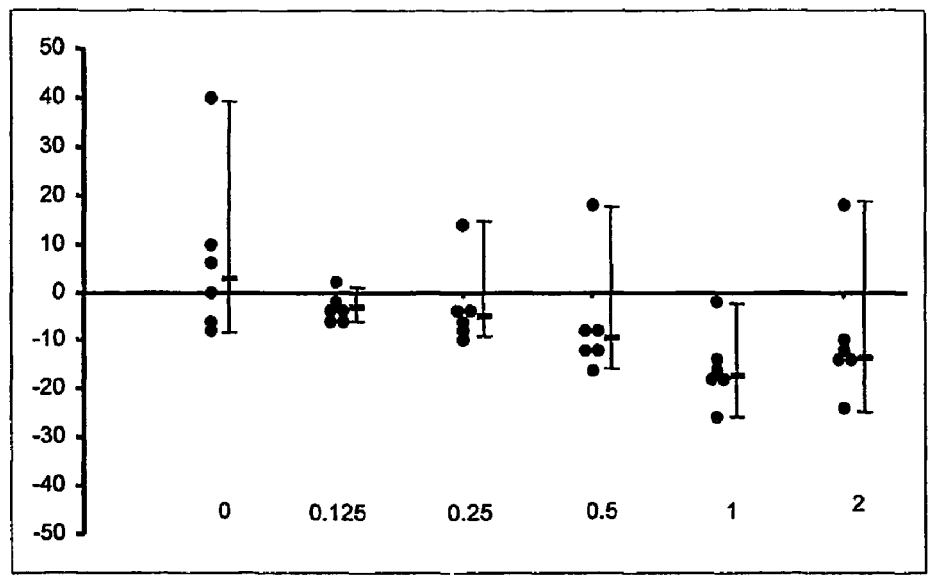

Figure 1. Dose dependence of the ICP reducing effect of Compound II during a 10 min infusion period. X-axis : Dose (mg/kg/min) ; Y-axis : Change in ICP as percentage of initial value.

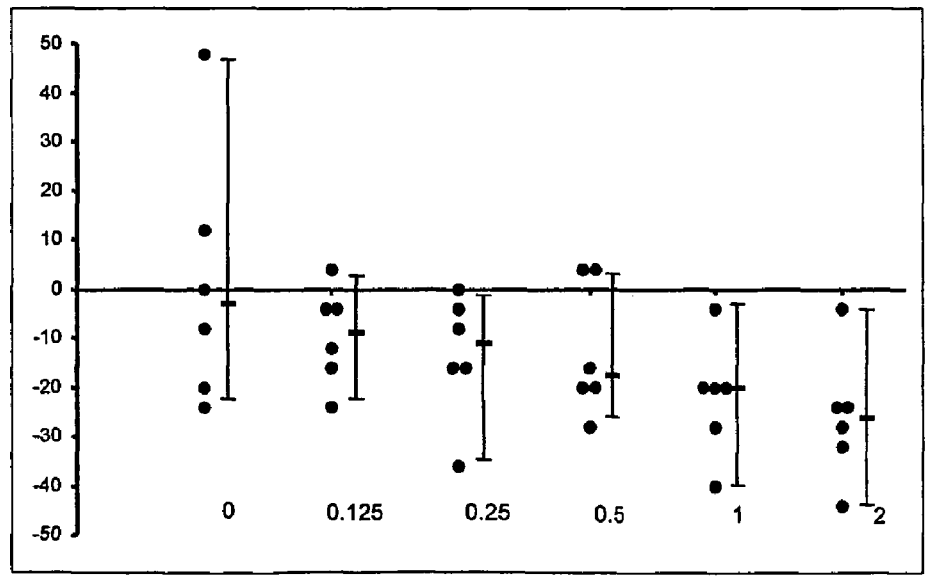

Figure 2. Dose dependence of the ICP reducing effect of Compound II during the 10 min post-treatment period following a 10 min infusion .

X-axis : Dose (mg/kg/min) ; Y-axis : Change in ICP as percentage of initial value.

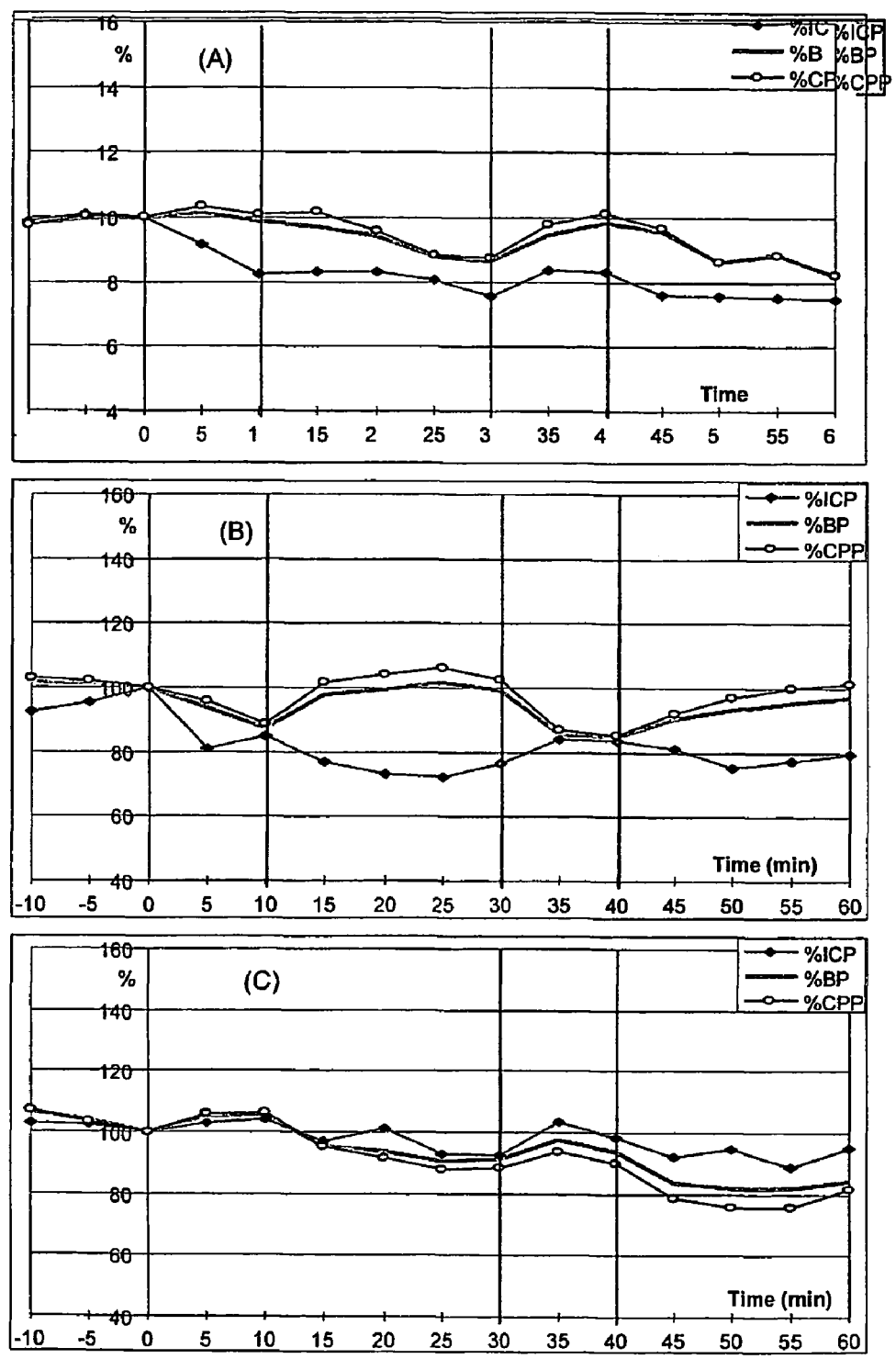
Figure 3: Time course of ICP, MABP and CPP in rats during 3 intermittent treatment periods of 10 min with respectively mannitol (Figure 3-A)(dose: 0.125 g/kg/min), Compound II (Figure 3-B) (dose: 1 mg/kg/min) and solvent (Figure 3-C)(10 % HP-

Figure 3 continued beta-CD, pH 4). Treatment was started at 20 min after severe head injury (time = 0) and was repeated at 30 min and 60 min. The curves connect the median value for the subsequent time points. Values are expressed as % of initial value.

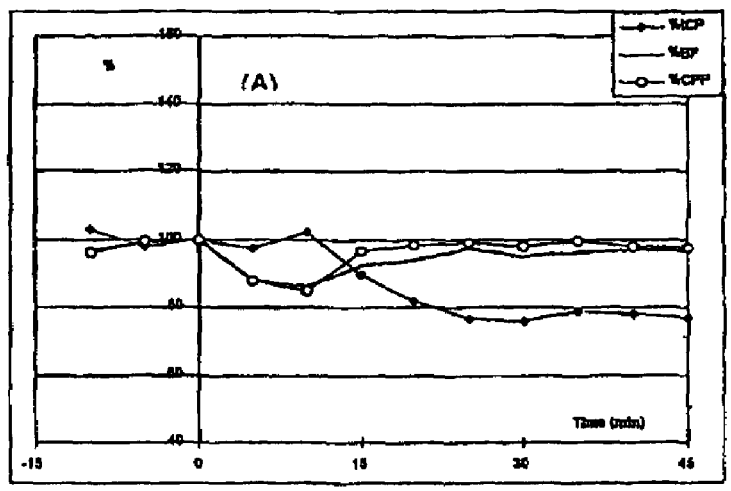

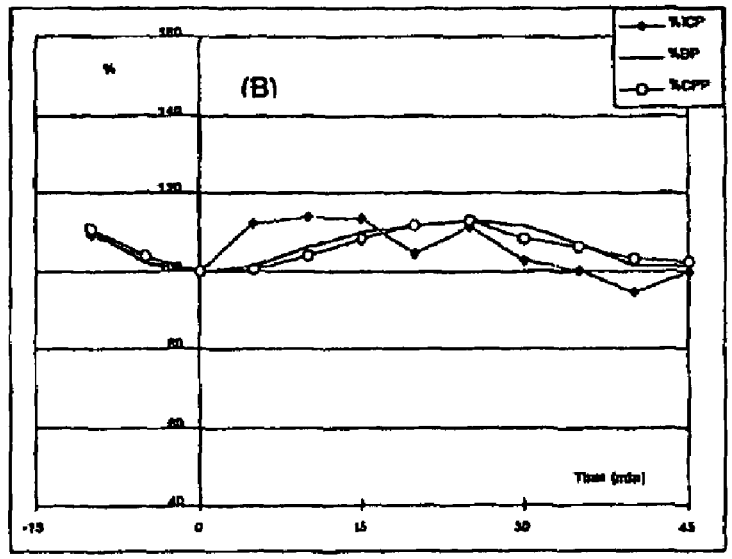

Figure 4: Time course of ICP, MABP and CPP in rabbits treated respectively with Compound II (Figure 4-A)(dose: 2 mg/kg/min during 10 min) or solvent (Figure 4-B)(2ml/min during 10 min). Treatment was started at 24 h after induction of a cortical cold lesion (time = 0). The curves connect the median value for the subsequent time points. Values are expressed as % of initial value.

SUBSTITUTED TETRACYCLIC IMIDAZOLE DERIVATIVES, PROCESSES FOR THEIR PREPARATION, PHARMACEUTICAL COMPOSITIONS COMPRISING THEM AND THEIR USE AS A MEDICINE

CROSS REFERENCE TO RELATED APPLICATIONS

This application is the national stage of Application No. PCT/EP02/06576, filed Jun. 11, 2002, which application claims priority from EP 01202260.4 filed Jun. 12, 2001.

FIELD OF THE INVENTION

The invention concerns novel substituted tetracyclic imidazole derivatives useful for the treatment of elevated intracranial pressure (ICP) and/or secondary ischaemia, in particular caused by brain injury, more in particular caused by traumatic (TBI) and non-traumatic brain injury, processes for their preparation, pharmaceutical compositions comprising them and their use as a medicine.

BACKGROUND OF THE INVENTION

TBI is a significant problem in developed countries. In the USA each year about 500,000 head injuries are severe enough to require hospitalization. Mortality is high and approximately 80,000 of these TBI-patients face a life-long debilitating loss of function, 5,000 develop epilepsy, and 2,000 live in a persistent vegetative state. TBI is the leading cause of death and disability in young adults today at an estimated cost in 1989 of over $25 billion per year.

Primary irreversible damage after brain trauma includes hemorrhage, contusion, neuronal necrosis and diffuse axonal injury. This damage, together with possible cardiovascular and respiratory depression, can induce acute secondary features including edema (vasogenic and/or cellular), secondary bleeding, alterations of cerebral blood volume (CBV), disturbed autoregulation of cerebral blood flow (CBF) and ischaemia. Edema, bleeding and an increase of CBV will increase the total brain volume and consequently the intracranial pressure (ICP). This in turn can lead to further progression of ischaemia, infarction, and, in severe cases, herniation of the brain stem with possible acute respiratory depression and death. Therapy in TBI should therefore be directed to the interruption of the pathologic cascade and the reduction of the brain volume and ICP. Prevention of a life threatening secondary increase in ICP, which often occurs e.g. in the post-acute phase after trauma or after cardiac resuscitation, is also a target for pharmacological treatment.

At present, the clinical tools for ICP reduction are limited. Standard treatment schedules include surgical drainage of the ventricles, blood pressure management, mannitol infusion, hyperventilation and high dose barbiturate therapy. Side effects of the non-surgical treatments include brain ischaemia, rebound effects on ICP and an increased risk for bacterial infections and sepsis. Also, various compounds with different mechanisms of actions (e.g. bradykinin antagonism, calcium antagonism, oxidative stress inhibition, glutamate receptor blockade and anti-epilepsy) have been tested in phase II and III clinical trials or are still under investigation (focus on outcome, not on ICP). Up to date no compound has been approved for the acute treatment of intracranial pressure (K. K. Jain, Chapter 4: Neuroprotection in Acute Trauma, 'Neuroprotection in CNS Disorders: Commercial Opportunities'. A Jain PharmaBiotech Report: 65-73, 2000). Obviously, there is a need for pharmaceuticals and/or therapies for the treatment of elevated intracranial pressure (ICP) and/or secondary ischaemia, in particular caused by brain injury, more in particular caused by traumatic brain injury (TBI).

The purpose of the present invention is to provide novel substituted tetracyclic imidazole derivatives having the property of acutely lowering a critically elevated intracranial pressure (ICP) and thereby preventing e.g. secondary ischaemia caused by brain injury.

WO 88/05306 (The General Hospital Corporation) discloses treating cranial fluid volume dysfunctions such as edema, hydrocephalus or glaucoma in an individual with compounds which are interactive with the atriopeptin receptors, or other nitrogen-containing guanylate cyclase activators, or compounds which are phosphodiesterase inhibitors.

WO 92/06981 (Schering Corporation) discloses substituted tricyclic imidazobenzazepine and imidazopyridoazepine derivatives having antiallergic and/or anti-inflammatory activity; the compounds posses PAF antagonistic properties and are useful for treating diseases when PAF is a factor in the disease, such as e.g. edema.

WO 92/22551 (Janssen Pharmaceutica) discloses substituted tricyclic imidazo-[2,1-b][3]benzazepine derivatives having a favourable antiallergic/antihistaminic activity.

WO 92/22553 (Janssen Pharmaceutica) discloses substituted tricyclic imidazo[1,2-a](pyrrolo, thieno or furano)[3,2-d]azepine derivatives having a favourable antiallergic/antihistaminic activity.

WO 94/13671 (Janssen Pharmaceutica) discloses substituted tricyclic triazolobenzazepine derivatives having antiallergic/antihistaminic activity.

WO 94/13680 (Janssen Pharmaceutica) discloses substituted tricyclic imidazo[1,2-a](pyrrolo, thieno or furano)[3,2-d]azepine derivatives having a favourable antiallergic/antihistaminic activity.

WO 94/13681 (Janssen Pharmaceutica) discloses substituted tricyclic triazolo(pyrrolo, thieno or furano)azepine derivatives having antiallergic/antihistaminic activity.

WO 95/02600 (Janssen Pharmaceutica) discloses substituted tricyclic imidazoazepines with favourable antiallergic properties.

WO 97/24356 (Janssen Pharmaceutica) discloses 1-(1,2-disubstituted piperidinyl)-4(fused imidazole)-piperidine derivatives for use as substance-P antagonists.

WO 97/34897 (Janssen Pharmaceutica) discloses substituted tricyclic fused imidazole derivatives as multidrug resistance modulators.

WO 99/13871 ((Janssen Pharmaceutica) discloses fused imidazole derivatives for improving oral bioavailability of pharmaceutical agents.

None of the above publications discloses the compounds according to the present invention and their use for acutely lowering a critically elevated intracranial pressure (ICP).

SUMMARY OF THE INVENTION

The present invention relates to novel substituted tetracyclic imidazole derivatives according to the general Formula (I)

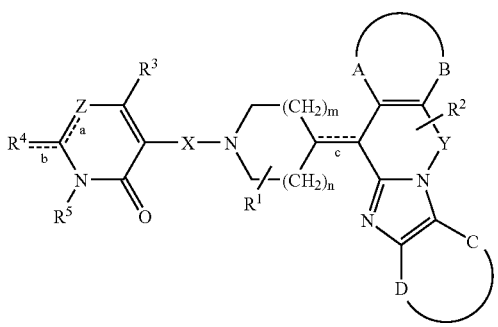

(I)

the pharmaceutically acceptable acid or base addition salts thereof, the stereochemically isomeric forms thereof and the N-oxide form thereof, wherein:

m is 1 or 2;
n is 0, 1 or 2;
a, b, c independently are a single or a double bond;
X is a covalent bond or a bivalent $C_{1-6}$alkanediyl radical wherein one or more —$CH_2$— groups may be optionally replaced with —O—, —S—, —C(=O)— or $NR^7$—; wherein:
  $R^7$ is hydrogen, alkyl, Ar, Ar-alkyl, Het, Het-alkyl, hydroxyalkyl, alkyloxy, alkyloxyalkyl, alkyloxyalkyloxyalkyl, aminoalkyl, mono- or dialkylaminoalkyl, formyl, alkylcarbonylaminoalkyl, alkylcarbonyloxyalkyl, alkyloxycarbonyl, alkyloxycarbonylalkyl, alkylaminocarbonyl, alkylaminocarbonylalkyl, hydroxyalkyloxyalkyl, aminocarbonyl, aminocarbonylalkyl, alkyloxycarbonyl, alkylcarbonyl or alkylcarbonyloxyalkyloxyalkyl;
Y is a bivalent $C_{1-4}$alkanediyl or $C_{2-4}$ alkenediyl radical;
Z is N, in which case a is a double bond and b is a single bond; or is N—$R^7$ in which case a is a single bond and $R^7$ is defined as above;
$R^1$, $R^2$ independently are hydrogen, hydroxy, alkyl, alkyloxy, Ar, Ar-alkyl, di(Ar-)alkyl, Het or Het-alkyl;
-A-B- independently is a bivalent radical of formula $$-E-CR^8=CR^8- \quad (a-1);$$

$$-CR^8=CR^8-E- \quad (a-2);$$

or $$-CR^8=CR^8-CR^8=CR^8- \quad (a-3);$$

wherein:
  $R^8$ each independently is hydrogen, halo, hydroxy, alkyl or alkyloxy;
  E is a bivalent radical of formula —O—, —S— or —$NR^7$— wherein $R^7$ is defined as above;
—C-D- independently is a bivalent radical of formula $$-CR^8=CR^8-CR^8=CR^8- \quad (b-1);$$

$$-N=CR^8-CR^8=CR^8- \quad (b-2);$$

$$-CR^8=N-CR^8=CR^8- \quad (b-3);$$

$$-CR^8=CR^8-N=CR^8- \quad (b-4);$$

or $$-CR^8=CR^8-CR^8=N- \quad (b-5);$$

wherein $R^8$ is defined as above;

$R^3$ is hydrogen, halo, hydroxy, alkyl, oxo, alkyloxy, Ar, Ar-alkyl, di(Ar—)alkyl, Het or Het-alkyl
$R^4$ is hydrogen, alkyl, amino, alkylamino, Ar-amino, Het-amino, Het-alkylamino, alkylcarbonylamino, Ar-carbonylamrino, Het-carbonylamino, alkylaminocarbonylamino, Ar-aminocarbonylamino, Het-aminocarbonylamino, alkyloxyalkylamino, Ar-oxyalkylamino or Het-oxyalkylamino;
$R^5$ is hydrogen or alkyl;
or $R^4$ and $R^5$ together may form a radical of Formula $$-M-CR^9=CR^{10}- \quad (c-1);$$

$$-CR^{10}=CR^9-M- \quad (c-2);$$

$$-M-CR^8R^8-CR^8R^8- \quad (c-3);$$

$$-CR^8R^8-CR^8R^8-M- \quad (c-4);$$

$$-CR^8=N-NR^7- \quad (c-5);$$

$$-NR^7-N=CR^8- \quad (c-6);$$

$$-CR^9=CR^{10}-CR^9=CR^{10}- \quad (c-7);$$

$$-CR^8R^8-CR^8R^8-CR^8R^8-M- \quad (c-8);$$

$$-M-CR^8R^8-CR^8R^8-CR^8R^8- \quad (c-9);$$

$$-CR^8R^8-CR^8=N-NR^7- \quad (c-10);$$

$$-NR^7-N=CR^8 CR^8R^8- \quad (c-11);$$

$$=N-CR^9=CR^{10}- \quad (c-12);$$

or $$-CR^9=CR^{10}-N= \quad (c-13);$$

wherein:
  $R^7$ and $R^8$ are defined as above;
  $R^9$, $R^{10}$ independently are hydrogen, alkyl, halo or haloalkyl;
    or $R^9$ and $R^{10}$ together may form a bivalent radical of formula —$CR^8=CR^8-CR^8=CR^8$— wherein $R^8$ is defined as above; and
  M is a bivalent radical of formula —$CH_2$—, —O—, —S— or —$NR^7$— wherein $R^7$ is defined as above;

BRIEF DESCRIPTION OF THE FIGURES

FIG. 1 graphically illustrates the does dependence of the ICP reducing effect of Compound II during a 10 minute infusion period. X-axis: Dose (mg/kg/min); Y-axis: Change in ICP as percentage of initial value.

FIG. 2 graphically illustrates the dose dependence of the ICP reducing effect of Compound II during the 10 minute post-treatment period following a 10 minute infusion. X-axis: Dose (mg(kg/min); Y-axis: Change in lCP as percentage of initial value.

FIG. 3 graphically illustrates the time course of lCP, MABP, and CPP in rats during 3 intermittent treatment periods of 10 minutes with respectively mannitol (FIG. 3-A) (dose: 0.125 g/kg/min), Compound II (FIG. 3-B) (dose: 1 mg/kg/min) and solvent (FIG. 3-C)(10% HP- beta-CD, pH 4. Treatment was started at 20 minutes after severe head injury (time=0) and was repeated at 30 minutes and 60 minutes. The curves connect the median values for the subsequent time points. Values are expressed as % of initial values.

FIG. 4 graphically illustrates the time course of ICP, MABP and CPP in rabbits treated respectively with Compound II (FIG. 4-A)(dose: 2 mg/kg/min during 10 minutes) FIG. 4-B)(2 ml/min during 10 minutes). Treatment was started 24 hours after the induction of a cortical cold lesion (time=0). The curves connect the median value for the subsequent time points. Values are expressed as % of initial value.

DETAILED DESCRIPTION OF THE INVENTION

In the framework of this application, Ar is a, homocycle selected from the group of naphthyl and phenyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl and mono- or dialkylaminocarbonyl. Preferably, Ar is a naphthyl or phenyl, each optionally substituted with 1 or 2 substituents, each substituent independently selected from the group of halo or alkyl.

In the framework of this application, Het is a monocyclic heterocycle selected from the group of pyrrolyl, pyrazolyl, imidazolyl, furyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuryl, isoindolyl and benzothienyl; each monocyclic and bicyclic heterocycle may optionally be substituted on a carbon atom with one or more halo, oxo, hydroxy, alkyl or alkyloxy radicals. Preferably, Het is pyridinyl, pyrazinyl, indolyl or isoindolyl, each radical optionally substituted on carbon atom with one or more oxo or alkyl radicals.

In the framework of this application, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with one or more halo, hydroxy, alkyloxy or oxo radicals. Preferably, alkyl is methyl, ethyl, n-propyl, n-butyl, n-pentyl or cyclohexylmethyl.

In the framework of this application, halo is a substituent selected from the group of fluoro, chloro, bromo and iodo and haloalkyl is a straight or branched saturated hydrocarbon radical having from 1 to 6 carbon atoms or a cyclic, saturated hydrocarbon radical having from 3 to 6 carbon atoms, wherein one or more carbonatoms are substituted with one or more halo-atoms. Preferably, halo is fluoro or chloro and preferably, haloalkyl is trifluoromethyl.

A preferred group of compounds are those compounds according to Formula (I), the pharmaceutically acceptable acid or base addition salts thereof, the stereochemically isomeric forms thereof and the N-oxide form thereof, in which m and n are both 1.

Another preferred group of compounds are those compounds according to Formula (I), the pharmaceutically acceptable acid or base addition salts thereof, the stereochemically isomeric forms thereof and the N-oxide form thereof, in which -A-B- is a bivalent radical of formula (a-2) or (a-3), wherein E is a bivalent radical of formula —S— or —NR$^7$— wherein R$^7$ is alkyl and wherein R$^8$ is hydrogen and —C-D- is a bivalent radical of formula (b-1) or (b-2) wherein R$^8$ is hydrogen and Y is a bivalent radical of formula —CH$_2$—, —CH$_2$—CH$_2$— or —CH=CH—.

Another group of preferred compounds of Formula (I) are those compounds according to Formula (I), the pharmaceutically acceptable acid or base addition salts thereof, the stereochemically isomeric forms thereof and the N-oxide form thereof, in which R$^1$ and R$^2$, each independently, are hydrogen, alkyl, Ar, Ar-alkyl, Het or Het-alkyl.

Yet another group of preferred compounds of Formula (I) are those compounds according to Formula (I), the pharmaceutically acceptable acid or base addition salts thereof, the stereochemically isomeric forms thereof and the N-oxide form thereof, in which X is a bivalent radical of formula —CH$_2$—, —CH$_2$CH$_2$—, —CH$_2$CH$_2$CH$_2$—, —CH$_2$CH$_2$CH$_2$CH$_2$— or, —CH$_2$CH$_2$CH$_2$CH$_2$CH$_2$— wherein one or more —CH$_2$— groups may be optionally replaced with —CO— or —NR$^7$— wherein R$^7$ is alkylcarbonyl.

Yet another group of preferred compounds of Formula (I) are those compounds according to Formula (a), the pharmaceutically acceptable acid or base addition salts thereof, the stereochemically isomeric forms thereof and the N-oxide form thereof, in which R$^3$ is alkyl or oxo, Z is NR$^7$ in which case a is a single bond and R$^7$ is alkyl, pyridinylalkyl, phenylalkyl or pyrazinylalkyl; and R$^4$ and R$^5$ together form a bivalent radical of Formula (c-1), (c-2), (c-3), (c-6), (c-7), (c-9), (c-11) or (c-12) wherein R$^7$ is alkyl, benzyl, pyridinylalkyl, alkyloxyalkyl, pyrazinylalkyl, alkyloxyalkyloxyalkyl, mono- or dialkylaminoalkyl, alkyloxycarbonylalkyl, hydroxyalkyl, isoindol-1,3-dionyl, aminocarbonylalkyl, hydroxyalkyloxyalkyl, alkylcarbonyloxyalkyloxyalkyl; aminoalkyl, alkylcarbonylaminoalkyl or alkyloxyalkyl; and R$^8$ is hydrogen, alkyl, halo or haloalkyl.

Yet another group of preferred compounds of Formula (I) are those compounds according to Formula (I), the pharmaceutically acceptable acid or base addition salts thereof, the stereochemically isomeric forms thereof and the N-oxide form thereof, in which R$^9$ and R$^{10}$ together form a radical of formula —CR$^8$=CR$^8$—CR$^8$=CR$^8$— wherein R$^8$ is hydrogen.

Another group of preferred compounds of Formula (I) are those compounds according to Formula (I), the pharmaceutically acceptable acid or base addition salts thereof, the stereochemically isomeric forms thereof and the N-oxide form thereof, in which m is 1;

n is 1;

a, b, c independently ate a single or a double bond;

X is a bivalent C$_{1-5}$alkanediyl radical wherein one or more —CH$_2$— groups may be optionally replaced with —CO—, or —NR$^7$—; wherein R$^7$ is alkylcarbonyl Y is —CH$_2$—, —CH$_2$—CH$_2$— or —CH=CH—;

Z is N, in which case a is a double bond and b is a single bond, or is NR$^7$ in which case a is a single bond and R$^7$ is selected from the group of alkyl, pyridinylalkyl, phenylalkyl and pyrazinylalkyl;

R$^1$, R$^2$ independently are hydrogen, alkyl, benzyl, naphthylmethyl, isoindolyl and phenyl;

-A-B- independently is a bivalent radical of formula

—CR$^8$=CR$^8$-E-  (a-2);

or

—CR$^8$=CR$^8$—CR$^8$=CR$^8$—  (a-3);

wherein

R$^8$ is hydrogen;

E is a bivalent radical of formula —S— or —NR$^7$— wherein R$^7$ is alkyl;

—C-D- independently is a bivalent radical of formula $$-CR^8=CR^8-CR^8=CR^8- \quad (b-1);$$

or $$-N=CR^8-CR^8=CR^8- \quad (b-2);$$

wherein R$^8$ is hydrogen;
R$^3$ is alkyl or oxo;
R$^4$ is amino, alkylamino, pyridinylalkylamino, phenylcarbonylamino, alkylaminocarbonylamino or alkyloxyalkylamino;
R$^5$ is alkyl;
or R$^4$ and R$^5$ together may form a radical of Formula $$-M-CR^9=CR^{10}- \quad (c-1);$$

$$-CR^{10}=CR^9-M- \quad (c-2);$$

$$-M-CR^8R^8-CR^8R^8- \quad (c-3);$$

$$-NR^7-N=CR^8- \quad (c-6);$$

$$-CR^8=CR^8-CR^8=CR^8- \quad (c-7);$$

$$-M-CR^8R^8-CR^8R^8-CR^8R^8- \quad (c-9);$$

$$-NR^7-N=CR^8-CR^8R^8- \quad (c-11);$$

$$=N-CR^9=CR^{10}- \quad (c-12);$$

wherein
R$^7$ is alkyl, benzyl, pyridinylalkyl, alkyloxyalkyl, pyrazinylalkyl, alkyloxyakyloxyalkyl, mono- or dialkylaminoalkyl, alkyloxycarbonylalkyl, hydroxyalkyl, isoindol-1,3-dionyl, aminocarbonylalkyl, hydroxyalkyloxyalkyl, alkylcarbonyloxyalkyloxyalkyl; aminoalkyl, alkylcarbonylaminoalkyl or alkyloxyalkyl;
R$^8$ is hydrogen, alkyl, halo or haloalkyl;
R$^9$, R$^{10}$ independently are hydrogen, alkyl, halo or haloalkyl;
or R$^9$ and R$^{10}$ together may form a radical of formula —CR$^8$=CR$^8$—CR$^8$=CR$^8$— wherein R$^8$ is hydrogen; and
M is a bivalent radical of formula —O—, —S— or —NR$^7$—, wherein R$^7$ is alkyl.

More specifically, the compound 3-[2-[4-(11,12-dihydro-6H-benzimidazo [2,1-b][3]benzazepin-6-yl)-2-(phenylmethyl)-1-piperidinyl]ethyl]-2,10-dimethyl pyrimido[1,2-a]benzimidazol-4(10H)-one, the pharmaceutically acceptable acid or base addition salts thereof, the stereochemically isomeric forms thereof and the N-oxide form thereof, are most preferred.

The pharmaceutically acceptable acid addition salts are defined to comprise the therapeutically active non-toxic acid addition salt forms which the compounds according to Formula (I) are able to form. Said acid addition salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to Formula (I) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to Formula (I) as well as the salts thereof, are able to form. Such solvates are, for example, hydrates and alcoholates.

Among the acid addition salts, the compound 3-[2-[4-(11,12-dihydro-6H-benzimidazo[2,1-b][3]benzazepin-6-yl)-2-(phenylmethyl)-1-piperidinyl]ethyl]-2,10-dimethylpyrimido [1,2-a]benzimidazol-4(10H)-one (E)-2-butenedioate (2:3) hydrate (1:1) including all stereoisomeric forms thereof is the most preferred compound.

Particulary preferred compounds are the (A)[(2α, 4β)(A)] enantiomer, the (B)[(2α, 4β)(A)] enantiomer and a mixture thereof, of the compounds 3-[2-[4-(11,12-dihydro-6H-benzimidazo[2,1-b][3]benzazepin-6-yl)-2-(phenylmethyl)-1-piperidinyl]ethyl]-2,10-dimethyl pyrimido[1,2-a]benzimidazol-4(10H)-one and 3-[2-[4-(11,12-dihydro-6H-benzimidazo[2,1-b][3]benzazepin-6-yl)-2-(phenylmethyl)-1-piperidinyl]ethyl]-2,10-dimethyl pyrimido [1,2-a]benzimidazol-4(10H)-one (E)-2-butenedioate (2:3) hydrate (1:1).

The N-oxide forms of the compounds according to Formula (I) are meant to comprise those compounds of Formula (I) wherein one or several nitrogen atoms are oxidized to the so-called N-oxide, particularly those N-oxides wherein one or more nitrogens of the piperidinyl radical in Formula (I) are N-oxidized.

The term "stereochemically isomeric forms" as used herein defines all possible isomeric forms which the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chiraliity and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When the bond at c is a single bond, compounds of Formula (I) and some of the intermediate compounds have at least two stereogenic centers in their structure. When $R^1$ is other than hydrogen, the monocyclic N-ring in Formula (I) has a further stereogenic center. This may lead to 8 stereochemically different structures.

The compounds of Formula (I) as prepared in the processes described below may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Some of the compounds of Formula (I) may also exist in their tautdmeric form. Such forms although not explicitly indicated in the above formula are intended to be included within the scope of the present invention. For instance, compounds of Formula (I) wherein $R^5$ is H may exist in their corresponding tautomeric form.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has, chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an, acid group which is esterified or amidated. Included in such esterified acid groups are groups of the formula —COOR$^x$, where $R^x$ is a $C_{1-6}$alkyl, phenyl, benzyl or one of the following groups:

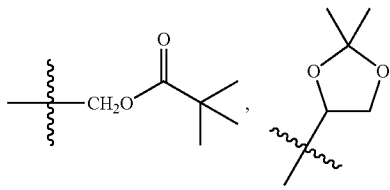

Amidated groups include groups of the formula —CONR$^y$R$^z$, wherein R$^y$ is H, $C_{1-6}$alkyl, phenyl or benzyl and R$^z$ is —OH, H, $C_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to the invention have surprisingly been shown to be suitable for the treatment of elevated intracranial pressure (ICP), in particular critically elevated ICP and/or secondary ischaemia, in particular caused by brain injury, more in particular either caused by traumatic brain injury (TBI) or non-traumatic brain injury, e.g. by stroke or cold lesion. The present invention thus also relates to compounds of Formula (I) as defined hereinabove, the pharmaceutically acceptable acid or base addition salts thereof, the stereochemically isomeric forms thereof and the N-oxide form thereof, for use as a medicine.

In vivo studies can be used to evaluate the activity of the present compounds. To this extent, a clinically relevant rat model for traumatic brain injury (Closed Head Injury-model) was developed and used to test the compounds according to the invention (K. Engelborghs et al., *Temporal changes in intracranial pressure in a modified experimental model of closed head injury, J. Neurosurg.* 89: 796-806, 1998; K. van Rossem et al., *Brain oxygenation after experimental closed head injury, Adv. Exp. Med. Biol.* 471: 209-215, 1999; K. Engelborghs et al., *Impaired autoregulation of cerebral blood flow in an experimental model of traumatic brain injury, J. Neurotrauma,* 17(8): 667-677, 2000). In one study intracranial hypertension was induced by a cortical cold lesion in rabbits.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. Most preferably,—for ease of quick administration—the aforementioned pharmaceutical composition is formulated as an injectable or perfusable solution or suspension.

Further, the present invention also relates to the use of a compound of Formula (I), the pharmaceutically acceptable acid or base addition salts thereof, the stereochemically isomeric forms thereof and the N-oxide form thereof, as well as any of the aforementioned pharmaceutical compositions thereof for the manufacture of a medicament for the treatment of elevated intracranial pressure (ICP) and secondary ischaemia.

The compounds according to the invention can generally be prepared by a succession of steps, each of which is known to the skilled person.

In particular, the compounds according to Formula (I) can be prepared by reacting an intermediate compound of Formula (II) with an intermediate compound of Formula (III) according to the following reaction scheme (1):

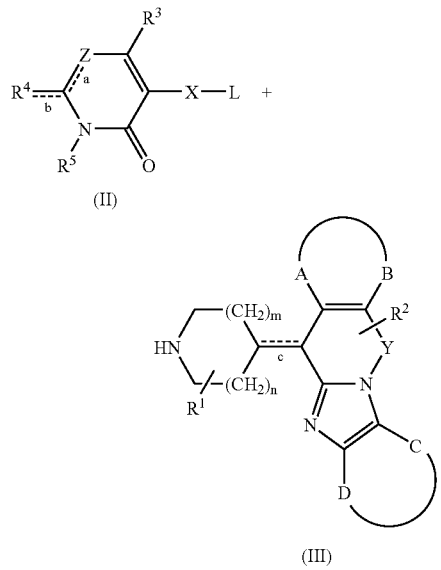

wherein all variables are defined as in Formula (I) and L represents any suitable reactive leaving group, in particular an halogen, such as chloro, bromo or iodo or a sulfonyloxy, such as methanesulfonyloxy or 4-methylbenzenesulfonyloxy. The reaction can be performed in a reaction-inert solvent, in particular a chlorinated hydrocarbon, for example dichloromethane, an alcohol, for example ethanol, or a ketone, for example MIBK, and in the presence of a suitable base, in particular sodium carbonate, sodium hydrogen carbonate or triethylamine. Stirring may enhance the rate of the reaction. The reaction may conveniently be carried out at a temperature ranging between room temperature and reflux temperature.

The starting materials and the intermediate compounds of Formulas (II) and (III) are compounds that are either commercially available or may be prepared according to conventional reaction procedures generally known in the art. For example, intermediate compounds of Formula (II-a) may be prepared according to the following reaction scheme (2):

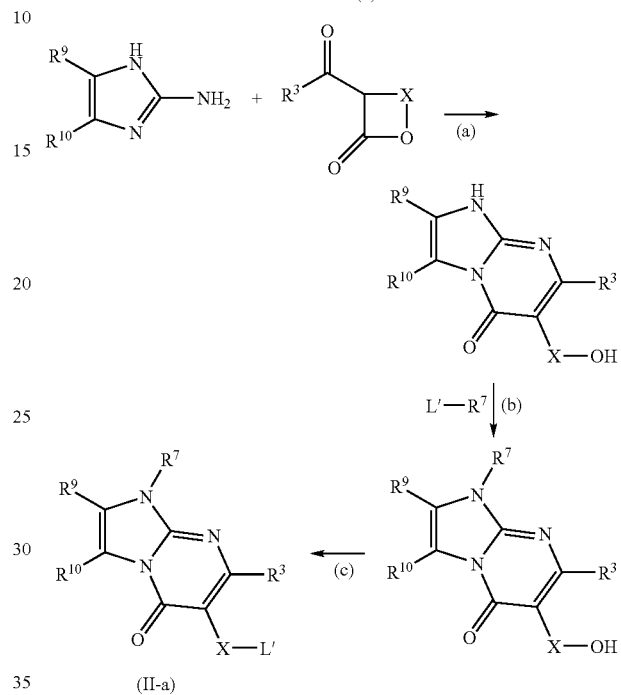

wherein all variables are defined as in Formula (I) and L' represents any suitable reactive leaving group, in particular an halogen, such as chloro, bromo or iodo or a sulfonyloxy, such as methanesulfonyloxy or 4-methylbenzenesulfonyloxy. The reaction scheme (2) comprises step (a) in which an appropriately $R^9$- and $R^{10}$-substituted 2-amino-imidazole is condensed with an alpha-acyllactone in the presence of a catalyst such as 4-methylbenzenesulfonic acid in a reaction-inert solvent such as 1,2 dimethoxyethane or xylene. The reaction may conveniently be carried out at a temperature ranging between room temperature and reflux temperature.

In a next step (b) the imidazo-pyrimidone derivative obtained in step (a) is reacted with an alkylating agent in the presence of a suitable base such as sodiumhydride, sodiumcarbonate, sodiumbicarbonate or the like, in an reaction-inert solvent such as DMF, DMA or THF. The reaction may conveniently be carried out at a temperature ranging between room temperature and reflux temperature.

In a further step (c) the hydroxy group is converted, for instance at ambient temperature, into a suitable leaving group L', for instance into a halo using an halogenating reagent such as phosphoroxychloride or thionylchloride or into a sulfonyloxy-group such as a methanesulfonyloxy group or a 4-methylbenzenesulfonyloxy group.

Intermediate compounds of Formulas (III-a), (III-b) and (III-c) may be prepared according to the following reaction scheme (3) wherein all variables are defined as in Formula (I) and Prot is defined as a N-protecting group, for example a tert-butyloxycarbonyl-group or a benzylgroup.

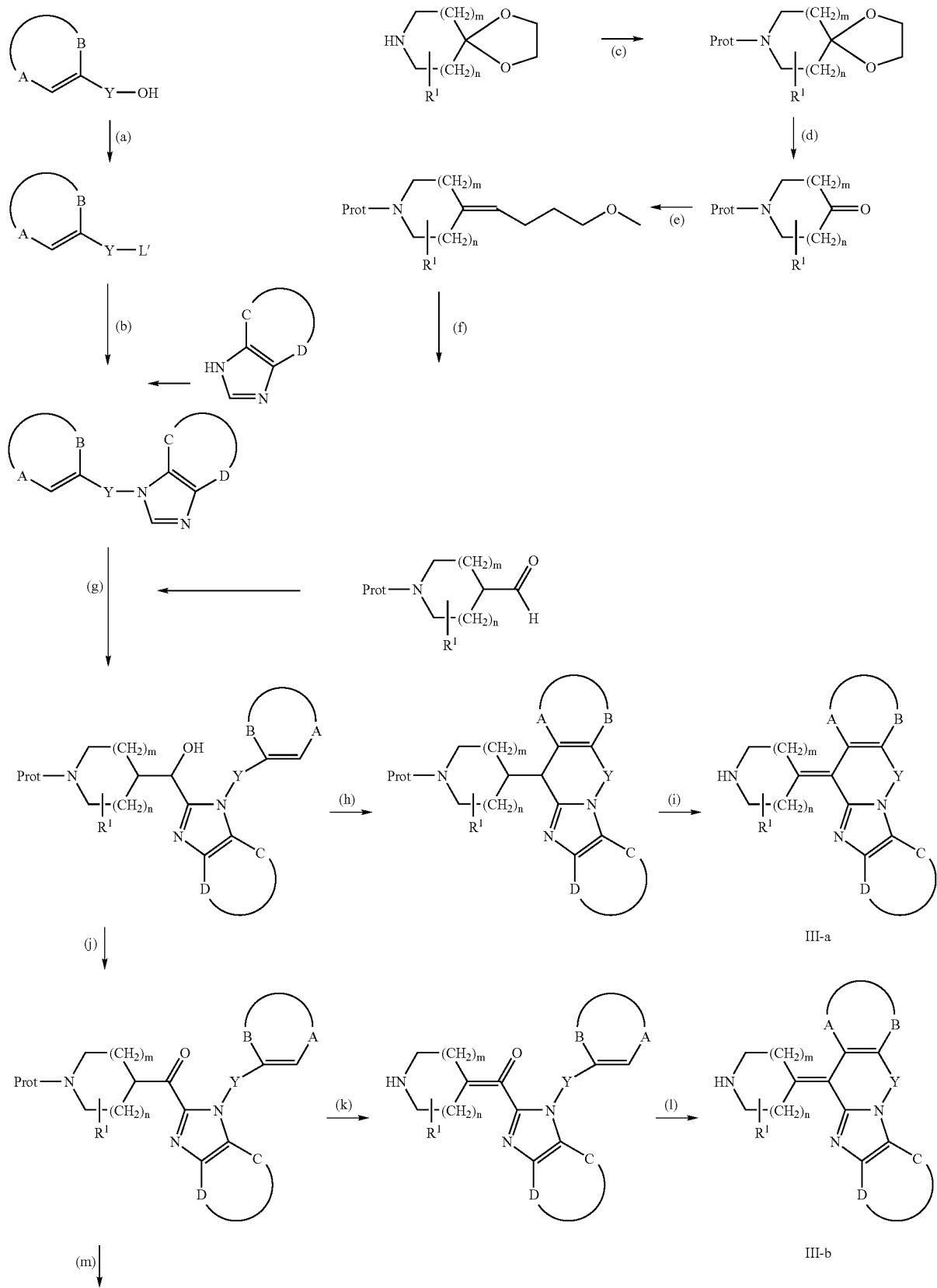

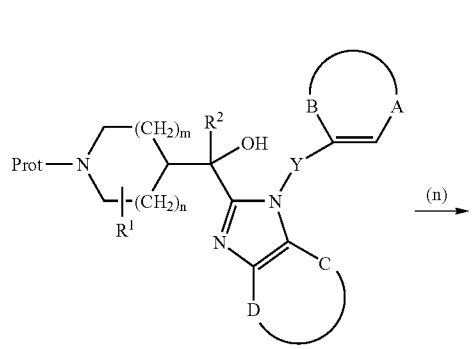 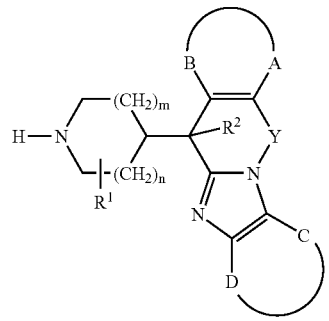 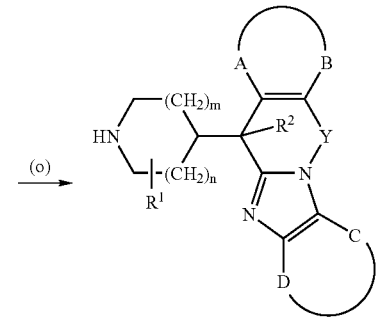

III-c

The reaction scheme comprises step (a) in which an appropriate alcohol is converted into a suitable leaving-group L', for instance into a halo using an halogenating reagent such as phosphoroxychloride or thionylchloride or into a sulfonyloxy-group such as a methanesulfonyloxy group or a 4-methylbenzenesulfonyloxy group. The reaction may conveniently be carried out at a temperature below room temperature, preferably with additional cooling means, such as a water ice bath.

In a next step (b) the mesylate obtained in step (a) is reacted with an appropriate imidazole derivative. The reaction can be performed in a reaction-inert solvent such as, for example, ethanol, MIBK or DMF, and in the presence of a suitable base such as, for example, sodium hydride, sodium carbonate, sodium hydrogen carbonate or triethylamine. Stirring may enhance the rate of the reaction. The reaction may conveniently be carried out at a temperature ranging between room temperature and reflux temperature.

For the second part of the intermediate compound, in a step (c) the aliphatic nitrogen containing ring system (e.g. a piperidine or pyrrolidine) is protected with an appropriate N-protecting group such as a tert-butyloxycarbonyl group or a benzyl group. The reaction can be performed in a reaction-inert solvent, in particular a chlorinated hydrocarbon, for example dichloromethane, an alcohol, for example ethanol, or a ketone, for example MIBK, and in the presence of a suitable base, in particular sodium carbonate, sodium hydrogen carbonate or triethylamine. Stirring may enhance the rate of the reaction as well as the addition of a catalyst such as potassium iodide. The reaction may conveniently be carried out at a temperature ranging between room temperature and reflux temperature.

In a further step (d) conversion of the cyclic ketal obtained in step (c) into the corresponding ketone can be performed by art-known methods such as the use of a diluted acid as a solvent in particular hydrochloric acid, sulfuric acid and the like. The reaction may conveniently be carried out at a temperature ranging between room temperature and reflux temperature.

In a further step (e) homologation of the ketone obtained in step (d) is carried out with a appropriate Wittig reagent such as (methoxymethyl)triphenyl-phosphonium chloride or (methoxymethyl)triphenyl-phosphonium bromide in the presence of a suitable base such as lithiumdiisopropylamide, potassium-tert-butoxide, or n-butyllithium, in an reaction-inert solvent such as THF. The reaction may conveniently be carried out at a temperature below room temperature, preferably at $-78°$ C.

Next, in step (f) the vinyl-ether obtained in step (e) is converted into the corresponding aldehyde in an way similar to step (d).

In a further step (g) the aldehyde obtained in step (f) is reacted with the imidazole derivative originated from step (b) in the presence of a strong base such as lithiumdiisopropylamine or n-butyllithium in an reaction-inert solvent such as THF. The reaction may conveniently be carried out at a temperature below room temperature, preferably at $-78°$ C.

Next, in step (h) a cyclization reaction is conveniently conducted by treating the alcohol derivative obtained in step (g) with an appropriate (Lewis) acid such as, for example, aluminiumtrichloride, methanesulfonic acid or trifluoromethanesulfonic acid. The reaction may conveniently be carried out at a temperature ranging between room temperature and about $150°$ C., above which decomposition may occur. It should be noted that only those intermediate compounds wherein the protecting group is stable under the given reaction conditions can be prepared according to the above mentioned reaction procedure; e.g. a tert-butyloxycarbonyl-group should not be used in combination with trifluoromethanesulfonic acid.

Finally, in step (i) the protecting group is removed from the nitrogen ring, e.g. by means of catalytic hydrogenation in case of a benzyl protecting group. Said catalytic hydrogenation reaction can be conducted following art-known procedures, e.g. stirring in a reaction-inert solvent, e.g. methanol, in the presence of a suitable catalyst, e.g. palladium-on-carbon and in the presence of hydrogen; optionally the temperature may be elevated in a range between room temperature and the reflux temperature of the reaction mixture and, if desired, the pressure of the hydrogen gas may be raised.

Intermediate compounds of Formula (III-b), comprising a double bond at position 6 of the tetracyclic ring system may be obtained using a procedure in which the alcohol derivative obtained in step (g) is converted into a ketone by oxidation with a suitable reagent such as e.g. manganese(IV)oxide in a reaction inert solvent such as trichloromethane or acetic acid (step j). The reaction may conveniently be carried out at a temperature ranging between room temperature and reflux temperature. Removal of the N-protecting group (step (k)) and subsequently cyclization (step (l)) is performed as previously described for respectively step (i) and step (h).

Intermediate compounds of Formula (III-c) may be obtained using a procedure in which a Grignard reagent $R^2$-X such as methylmagnesium chloride or an organometallic compound such as methyllithium is reacted with the ketone obtained in step (j) in a suitable solvent such as THF to give the corresponding alcohol (step (m)). The reaction may conveniently be carried out at a temperature below room temperature, preferably at −78° C. The subsequent cyclization reaction (step n) is conveniently conducted by art-known methodologies as described for step (h). The protecting group is subsequently removed from the nitrogen ring (step o) using a procedure similar to step (i).

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, intermediate compounds of Formula (III-a), (III-b) and (III-c) and final compounds according to Formula (I) may be separated into their enantiomeric forms.

The following examples illustrate the present invention without being limited thereto.

Experimental Part

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The isolation method is described in detail below.

For example, for the compound pyrimido[1,2-a]benzimidazol-4(10H)-one, 3-[2-[4-(11,12-dihydro-6H-benzimidazo[2,1-b][3]benzazepin-6-yl)-2-(phenylmethyl)-1-piperidinyl]ethyl]-2,10-dimethyl, the 8 possible stereochemical isomeric forms are defined as follows:

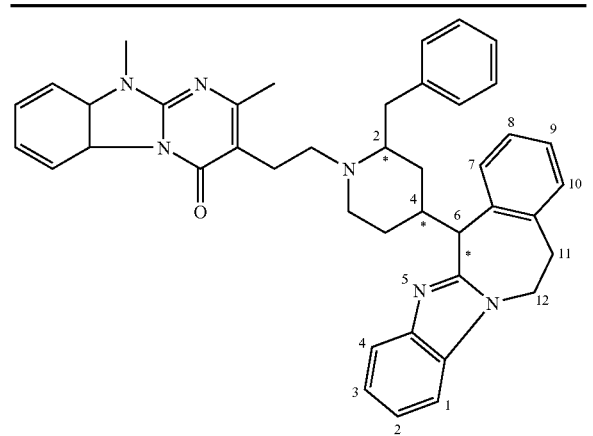

| CIS-forms | (2α, 4α)(A) | (A)[(2α, 4α)(A)] |
| | | (B)[(2α, 4α)(A)] |
| | (2α, 4α)(B) | (A)[(2α, 4α)(B)] |
| | | (B)[(2α, 4α)(B)] |
| TRANS-forms | (2α, 4β)(A) | (A)[(2α, 4β)(A)] |
| | | (B)[(2α, 4β)(A)] |
| | (2α, 4β)(B) | (A)[(2α, 4β)(B)] |
| | | (B)[(2α, 4β)(B)] |

Hereinabove and hereinafter, "DMF" is defined as N,N-dimethylformamide, "DIPE" is defined as diisopropyl ether, "THF" is defined as tetrahydrofurane, "MIBK" is defined as methyl isobutylketone, "DIPA" is defined as diisopropylamine.

A. Preparation of the Intermediate Compounds

EXAMPLE A1 a) Preparation of Intermediate 1

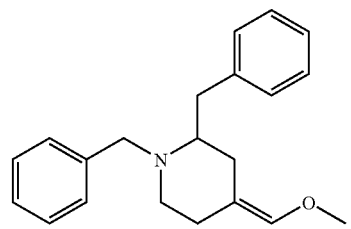

Use dry glassware. A mixture of (methoxymethyl)triphenylphosphoniumchloride (0.35 mol) in THF p.a. (mol. sieves) (2l) was stirred at −50° C. under N₂ flow. BuLi, 2.5 M/hexane (0.35 mol) was added dropwise and the mixture was stirred at −25° C. for 30 min. A solution of 1,2-bis(phenylmethyl)-4-piperidinone (0.35 mol) in THF was added dropwise at −25° C. The mixture was allowed to warm to room temperature, then stirred at room temperature overnight and decomposed with water. The organic solvent was evaporated. The aqueous concentrate was extracted with CH₂Cl₂. The organic layer was separated, dried (MgSO₄), filtered and the solvent was evaporated. The residue was purified by column chromatography over silica gel (eluent: CH₂Cl₂/CH₃OH 97.5/2.5). The pure fractions were collected and the solvent was evaporated. Yielding: 121 g of 4-(methoxymethylene)-1,2-bis(phenylmethyl)piperidine enantiomeric mixture (intermediate 1) (100%).

b) Preparation of Intermediate 2

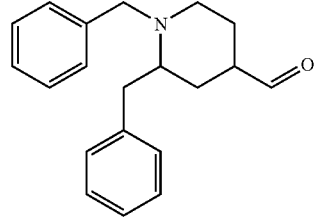

A mixture of intermediate 1 (0.35 mol) in THF (500 ml) was stirred till complete dissolution. H₂O (900 ml) and then HCl p.a. 38% (100 ml) were added. The mixture was stirred and refluxed for 3 hours. The organic solvent was evaporated. The aqueous concentrate was alkalized with K₂CO₃ and extracted with CH₂Cl₂. The organic layer was separated, dried (MgSO₄), filtered and the solvent was evaporated. The residue was purified by column chromatography over silica gel (eluent: CH₂Cl₂/CH₃OH 97/3). The pure fractions were collected and the solvent was evaporated. Yielding: 81 g of 1,2-bis(phenylmethyl)₄-piperidinecarboxaldehyde enantiomeric mixture (intermediate 2) (79%).

c) Preparation of Intermediate 3

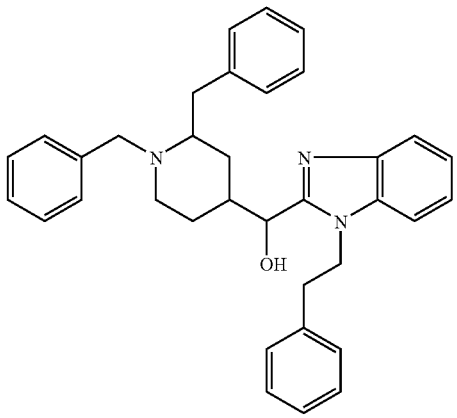

A mixture of DIPA (0.33 mol) in THF p.a. (previously dried on mol. sieves) (2l) was stirred at –78° C. under N₂ flow. BuLi, 2.5M/hexane (0.276 mol) was added dropwise. The mixture was stirred at –78° C. for 15 min. A solution of 1-(2-phenylethyl)-1H-benzimidazole (0.276 mol) in THF was added dropwise. The mixture was stirred at –78° C. for 1 hour. A solution of intermediate 2 (0.276 mol) in THF was added dropwise. The mixture was stirred at –78° C. for 1 hour, then allowed to warm to room temperature, stirred at room temperature overnight and then decomposed with water. The organic solvent was evaporated. The aqueous concentrate was extracted with CH₂Cl₂. The organic layer was separated, dried (MgSO₄), filtered and the solvent was evaporated. The residue was purified by column chromatography over silica gel (eluent: CH₂Cl₂/CH₃OH 95/5 to 90/10). The pure fractions were collected and the solvent was evaporated. Yielding: 113 g of α-[1,2-bis(phenylmethyl)-4-piperidinyl]-1-(2-phenylethyl)-1H-benzimidazole-2-methanol (intermediate 3)(79%).

d) Preparation of Intermediate 4

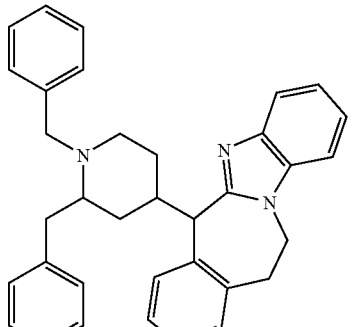

[(2α,4β)(A)]

A mixture of intermediate 3 (0.22 mol) in trifluoromethanesulfonic acid (750 ml) was stirred at 110° C. for 7 hours. The mixture was cooled, poured out on ice, alkalized with NaOH 50% and extracted with CH₂Cl₂. The organic layer was separated, dried (MgSO₄), filtered and the solvent was evaporated. The residue was crystallized from CH₃CN. The mixture was filtered. The precipitate and the filtrate was purified separately by column chromatography over silica gel (eluent: CH₂Cl₂/CH₃OH 98.5/1.5 to 95/5). Four pure fractions were collected and their solvents were evaporated. The residues were crystallized from CH₃CN. The precipitates were filtered off and dried. Yielding: 16 g of fraction 1 [(2a, 4β)(A)]-6-[1,2-bis(phenylmethyl)-4-piperidinyl]-11,12-dihydro-6H-benzimidazo[2,1-b][3]benzazepine (intermediate 4) (14.6%), 19.5 g of fraction 2 [(2a; 4β)(B)]-6-[1,2-bis(phenylmethyl)₄-piperidinyl]-11,12-dihydro-6H-benzimidazo[2,1-b][3]benzazepine (17.8%), 8.66 g fraction 3 [(2α, 4α)(A)]-6-[1,2-bis(phenylmethyl)-4-piperidinyl]-11,12-dihydro-6H-benzimidazo[2,1-b][3]benzazepine (7.9%) and 7.74 g of fraction 4 [(2a, 4α)(B)]-6-[1,2-bis(phenylmethyl)-4-piperidinyl]-11,12-dihydro-6H-benzimidazo[2,1-b][3]benzazepine (8.9%).

e) Preparation of Intermediate 5

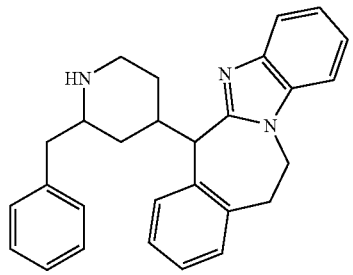

A mixture of intermediate 4 (0.0305 mol) in methanol (150 ml) was hydrogenated at 50° C. overnight with Pd/C 10% (1 g) as a catalyst. After uptake of H₂ (1 equiv), the catalyst was filtered off and the filtrate was evaporated. The residue was crystallized from CH₃CN. The precipitate was filtered off and dried. Yielding: 11.66 g of [(2a, 4β)(A)]-11,12-dihydro-6-[2-(phenylmethyl)-4-piperidinyl]-6H-benzimidazo[2,1-b][3]benzazepine (intermediate 5) (94%).

EXAMPLE A2 a) Preparation of Intermediate 6

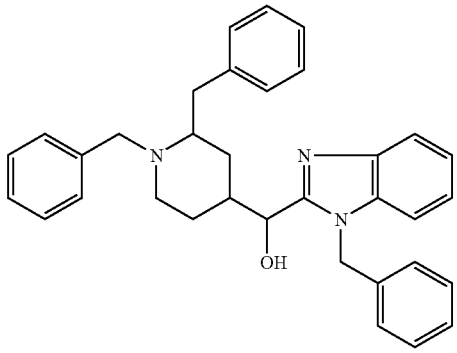

Use dry glassware. A mixture of DIPA (0.22 mol) in THF p.a. (previously dried on mol. sieves) (1400 ml) was stirred at –70° C. under N₂ flow. BuLi 2.5M (0.185 mol) was added dropwise and the mixture was stirred at –70° C. for 15 min. 1-(phenylmethyl)-1H-benzimidazole (0.185 mol) dissolved in THF was added dropwise at –70° C. and the mixture was stirred at –70° C. for 1 hour. Intermediate 2 (0.185 mol) dissolved in THF was added dropwise at –70° C. The mixture was stirred at –70° C. for 1 hour, then brought slowly to room temperature, stirred at room temperature overnight and decomposed with H₂O. The organic solvent was evaporated. The aqueous concentrate was extracted with CH₂Cl₂. The organic layer was separated, dried (MgSO₄), filtered and the solvent was evaporated. The residue was purified by column chromatography over silica gel (eluent: CH₂Cl₂/CH₃OH 95/5). The pure fractions were collected and the solvent was evaporated. Yielding: 91 g of intermediate 6 (98%).

b) Preparation of Intermediate 7

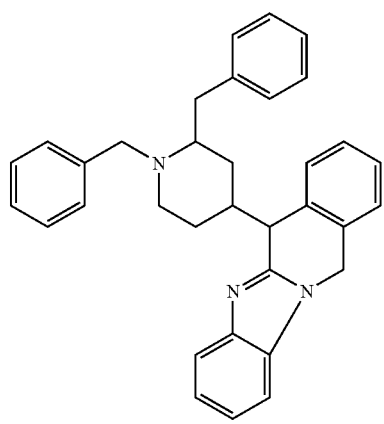

A mixture of intermediate 6 (0.18 mol) in trifluoromethanesulfonic acid (700 ml) was stirred at 120° C. under N₂ flow for 18 hours. The mixture was cooled, poured out on ice, alkalized with NaOH 50% and extracted with CH₂Cl₂. The organic layer was separated, dried (MgSO₄), filtered and the solvent was evaporated. The residue was purified by column chromatography over silica gel (eluent: CH₂Cl₂/(CH₃OH/NH₃) 99/1). The pure fractions were collected and the solvent was evaporated. Yielding: 40 g of intermediate 7 (46%).

c) Preparation of Intermediate 8

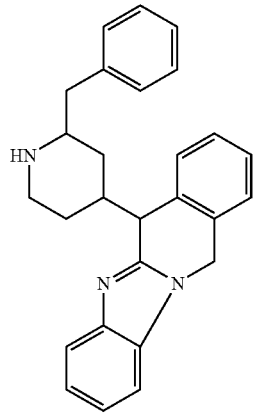

[(2α,4β)(A)]

and Preparation of Intermediate 9

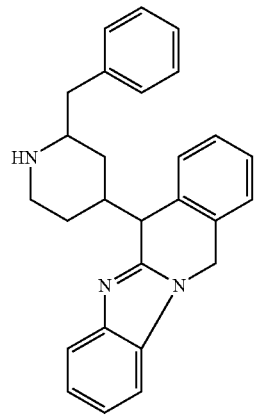

CIS

A mixture of intermediate 7 (0.081 mol) in methanol (200 ml) was hydrogenated at 50° C. with Pd/C 10% (2 g) as a catalyst. After uptake of H₂ (1 equiv), the catalyst was filtered off and the filtrate was evaporated. This fraction was purified by column chromatography over silica gel (eluent: CH₂Cl₂/(CH₃OH/NH₃) 97/3). Two pure fractions were collected and their solvents were evaporated. Yielding: Fraction 1 and 12.5 g of intermediate 9 (cis isomers) (36%). Fraction 1 was crystallized from CH₃CN. The precipitate was filtered off and dried. Yielding: 4.44 g of intermediate 8 (14%)([(2α, 4β)(A)]-racemate.

EXAMPLE A3 a) Preparation of Intermediate 10

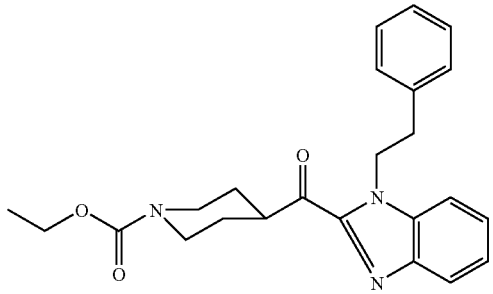

A mixture of DIPA (0.1 mol) in THF (100 ml) was stirred under N₂ flow. The mixture was cooled to −70° C. and BuLi, 2.5M/hexane (40 ml) was added portionwise. The temperature was allowed to reach −30° C., while stirring for 10 min. The mixture was cooled to −70° C. A solution of 1-(phenylethyl)-1H-benzimidazole (0.1 mol) in THF (50 ml) was added dropwise at this temperature and the mixture was stirred for 2 h at −70° C. Ethyl 4-formyl-1-piperidinecarboxylate (0.1 mol) was added dropwise and the mixture was stirred for 30 min at −70° C. The mixture was allowed to reach room temperature and stirring was continued for 30 min. The mixture was decomposed with water, then evaporated. The residue was stirred in water, and this mixture was extracted with CH₂Cl₂. The organic layer was separated, dried, filtered and the solvent was evaporated. The residue was purified by column chromatography over silica gel (eluent: CH₂Cl₂/CH₃OH 98/2). The pure fractions were collected and the solvent was evaporated. Yielding: 38 g of ethyl 4-[hydroxy[1-(2-phenyl-ethyl)-1H-benzimidazol-2-yl]methyl]-1-piperidinecarboxylate (intermediate 10).

b) Preparation of Intermediate 11

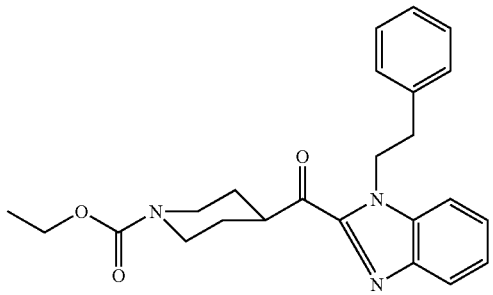

A mixture of intermediate 10 (0.011 mol) and MnO$_2$ (15 g) in CH$_2$Cl$_2$ (150 ml) was stirred overnight at room temperature. MnO$_2$ was filtered off over dicalite. The reaction was performed a second time with identical quantities. The mixture was stirred overnight. MnO$_2$ was filtered off over dicalite. The filtrate was evaporated. Yielding: 4.5 g ethyl 4-[[1-(2-phenylethyl)-1H-benzimidazol-2-yl]carbonyl]-1-piperdinecarboxylate (intermediate 11).

c) Preparation of Intermediate 12

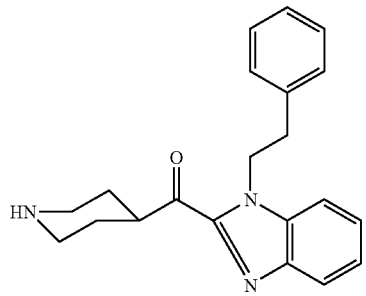

A mixture of intermediate 11 (0.011 mol) and HBr, 48% aq. (25 ml) was stirred for 10 h at 80° C. The solvent was evaporated. The residue was stirred in boiling. 2-propanol, cooled and the resulting precipitate was filtered off and dried. A sample (1 g) was recrystallized from ethanol. The crystals were filtered off and dried. Yielding: 0.5 g of [1-(2-phenylethyl)-1H-benzimidazol-2-yl] (4-piperidinyl)methanone dihydrobromide (intermediate 12) (mp. 261.9° C.).

d) Preparation of Intermediate 13

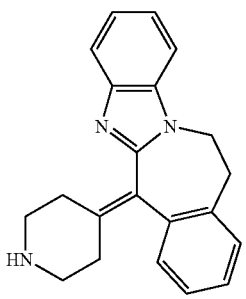

Trifluoromethanesulfonic acid (150 ml) was stirred under N$_2$ flow. Intermediate 12 (0.1 mol) was added portionwise and the resulting reaction mixture was stirred for 20 h at 100° C. (N$_2$ flow). The reaction mixture was cooled, poured out into ice (1 kg) and the resulting mixture was neutralized with NaOH 50%, while stirring and cooling. This mixture was extracted with CH$_2$Cl$_2$. Precipitation resulted. The organic layer was separated. The precipitate was filtered off and recrystallized from CH$_3$CN. The crystals were filtered off and recrystallized again from CH$_3$CN. The crystals were filtered off and dried. Yielding: 3.0 g of 11,12-dihydro-6-(4-piperidinylidene)-6H-benzimidazo[2,1-b][3]benzazepine trifluoromethanesulfonate (2:3). The separated organic liquor was combined with the mother layers, dried, filtered and the solvent was evaporated. The residue (37 g) was dissolved in water/ethanol, alkalized with 50% NaOH and extracted with CH$_2$Cl$_2$. The separated organic layer was dried (MgSO$_4$), filtered and the solvent was evaporated. The residue was stirred in 2-propanone/DIPE, then filtered off and dried. Yielding: 16.2 g of 11,12-dihydro-6-(4-piperidinylidene)-6H-benzimidazo[2,1-b][3]benzazepine (intermediate 13) (mp. 180.3° C.).

EXAMPLE A4 a) Preparation of Intermediate 14

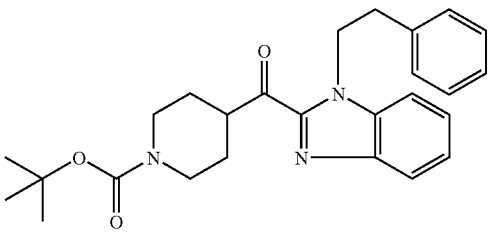

Use dry glassware. A mixture of DIPA (1.1 mol) in THF p.a. (previously dried on mol. sieves) (3000 ml) was stirred at −78° C. under N$_2$ flow. BuLi 1.5M in hexane (1.05 mol) was added dropwise at −70° C. and the mixture was stirred at −70° C. for 20 min. 1-(phenylethyl)-1H-benzimidazole (1 mol)-dissolved in THF was added dropwise at −78° C. and the mixture was stirred at −78° C. for 1 hour. 4-ethyl 1-(1,1-dimethyl)1,4-piperidinedicarboxylate (1.1 mol) dissolved in THF was added dropwise at −70° C. The mixture was stirred at −78° C. for 1 hour, then brought to room temperature, stirred at room temperature overnight and decomposed with H$_2$O. The organic solvent was evaporated. The aqueous concentrate was extracted with CH$_2$Cl$_2$. The organic layer was separated, dried (MgSO$_4$), filtered and the solvent was evaporated. The residue was crystallized from CH$_3$CN. The precipitate was filtered off and dried. Yielding: 350 g of intermediate 14 (81%).

b) Preparation of Intermediate 15

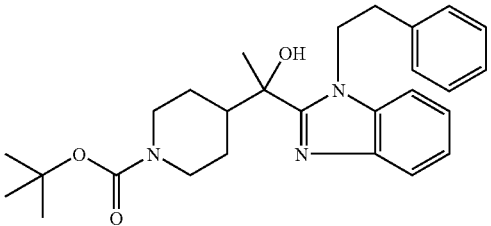

Reaction under N$_2$ atmosphere. Methylmagnesium chloride (0.0165 mol; 8.2 ml, 2.0 M/THF) was added dropwise to a solution of intermediate 14 (0.0150 mol) in THF (90 ml), stirred at room temperature. The resulting reaction mixture was stirred for 2 hours. Water was added. The organic solvent was evaporated and the aqueous concentrate was extracted with CH$_2$Cl$_2$. The separated organic layer was dried, filtered and the solvent evaporated. The residue (6 g) was crystallized from CH$_3$CN. The precipitate was filtered off and dried. Yielding: 4.3 g of intermediate 15 (64%).

c) Preparation of Intermediate 16

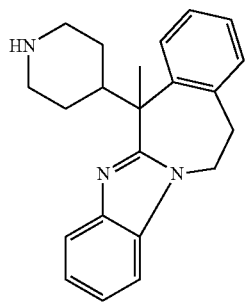

A mixture of intermediate 15 (0.0076 mol) in trifluoromethanesulfonic acid (29 in) was stirred for 48 hours at room temperature. The reaction mixture was poured out into water. This mixture was alkalized with K$_2$CO$_3$. The aqueous layer was extracted with CH$_2$Cl$_2$. The separated organic layer was dried, filtered and the solvent evaporated. The residue was purified by short open column chromatography over silica gel (eluent: CH$_2$Cl$_2$/(CH$_3$OH/NH$_3$) 90/10). The pure fractions were collected and the solvent was evaporated. Yielding: 2 g of intermediate 16 (79%).

EXAMPLE A5 a) Preparation of Intermediate 17

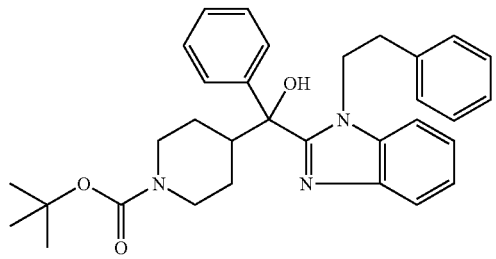

Reaction under N$_2$ atmosphere. Phenylmagnesium chloride (0.0440 mol) was added to a solution of intermediate 14 (0.0400 mol) in THF (200 ml), stirred at room temperature. The resulting reaction mixture was stirred for one hour. Water was added. The organic solvent was evaporated and the aqueous concentrate was extracted with CH$_2$Cl$_2$. The separated organic layer was dried, filtered and the solvent evaporated. This residue was combined with analogously obtained material and the whole (20 g) was crystallized from CH$_3$CN. The precipitate was filtered off and dried. Yielding: 20 g of intermediate 17 (98%).

b) Preparation of Intermediate 18

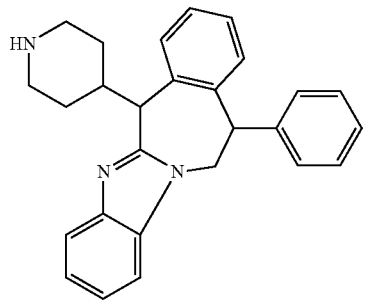

A mixture of intermediate 17 (0.0360 mol) in trifluoromethanesulfonic acid (120 ml) was stirred for 24 hours, going from 0° C. to room temperature. The reaction mixture was poured out into water. This mixture was alkalized with NaOH 50%, then extracted with CH$_2$Cl$_2$. The separated organic layer was dried, filtered and the solvent evaporated. The residue was crystallized from CH$_3$CN, filtered off, then purified by short open column chromatography over silica gel (eluent: CH$_2$Cl$_2$/(CH$_3$OH/NH$_3$) 90/10). The pure fractions were collected and the solvent was evaporated. Yielding: 11 g of intermediate 18 (78%). (mp. 270.7° C.)

EXAMPLE A6 a) Preparation of Intermediate 19

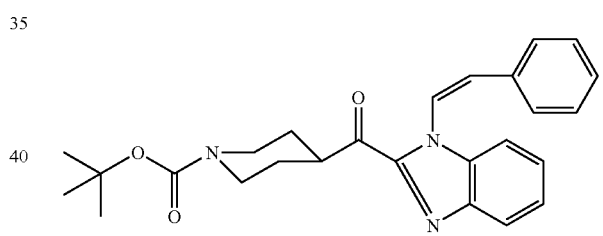

A mixture of 1-(2-phenylethenyl)-1H-benzimidazole (0.04 mol) in THF (100 ml) was stirred under N$_2$ flow and cooled to −70° C. BuLi, 2.5 M/hexane (0.04 mol) was added dropwise at −70° C. and stirring was continued for 30 min at −70° C. A solution of 4-ethyl 1-(1,1-dimethylethyl)-1,4-piperidinedicarboxylate (0.04 mol) in THF was added dropwise and the mixture was stirred for 1 h at −70° C. The temperature was allowed to reach room temperature and the mixture was decomposed with water, then extracted with CH$_2$Cl$_2$. The separated organic layer was dried (MgSO$_4$), filtered and the solvent was evaporated. The residue was purified by column chromatography over silica gel (eluent: CH$_2$Cl$_2$/CH$_3$CN 97/3 upgrading to 94/6). Two fractions were collected and the solvent was evaporated. The second fraction's residue was crystallized from DIPE/CH$_3$CN. The crystals were filtered off and dried. Yielding: 7.0 g of (1,1-dimethylethyl) (Z)-4-[[1-(2-phenylethenyl)-1H-benzimidazol-2-yl]carbonyl]-1-piperidinecarboxylate (41%) (intermediate 19). (mp. 155.8° C.)

b) Preparation of Intermediate 20

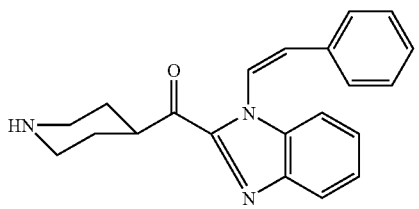

A mixture of intermediate 19 (0.043 mol) in trifluoroacetic acid (130 ml) was stirred for ½ hour at room temperature. The reaction mixture was poured out into diethylether. The precipitate was filtered off, washed with diethylether and dried. Yielding: 18 g of (Z)-[1-(2-phenylethenyl)-1H-benzimidazol-2yl](4-piperidinyl)methanone trifluoroacetate (1:1) (intermediate 20) (94.0%). (mp. 202.2° C.)

c) Preparation of Intermediate 21

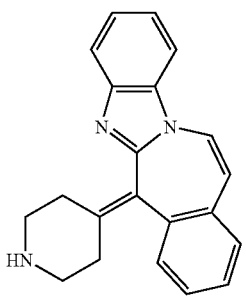

A mixture of intermediate 20 (0.0276 mol), AlCl$_3$ (0.187 mol) and NaCl (0.187 mol) was stirred for 1 hour at 150° C. (melt). The reaction mixture was decomposed in a mixture of ice, water and NaOH 50%. The mixture was extracted with dichloromethane and the organic layer was separated, dried, filtered and evaporated. The residue. 4.3 g) was purified on a glass filter over silica gel (eluent: CH$_2$Cl$_2$/(CH$_3$OH/NH$_3$) 90/10). The pure fractions were collected and the solvent was evaporated. The residue was converted into the (E)-2-butenedioic acid salt (2:3) in ethanol. The salt was filtered off and dried. Yielding: 1.8 g of 6-(4-piperidinylidene)-6H-benzimidazo[2,1-b][3]benzazepine (E)-2-butenedioate (2:3) (13.4%) (intermediate 21). (mp. 229.4° C.)

EXAMPLE A7 a) Preparation of Intermediate 22

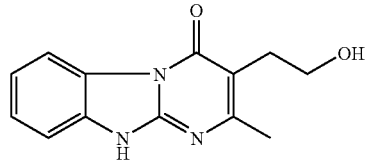

A mixture of 2-amine-1H-benzimidazole (0.04 mol), 3-acetyldihydro-2(3H)-furanone (0.53 mol) and 4-methylbenzenesulfonic acid (4 g) in xylene (930 ml) was stirred and refluxed overnight and then cooled. The precipitate was filtered off and stirred in H$_2$O (200 ml), Na$_2$CO$_3$ (5 g) and CH$_2$Cl$_2$ (500 ml). The precipitate was filtered off, boiled in CH$_3$OH, filtered off and dried. Yielding: 47.4 g of 3-(2-hydroxyethyl)-2-methyl-pyrimido[1,2-a]benzimidazol-4(10H)-one (intermediate 22).

b) Preparation of Intermediate 23

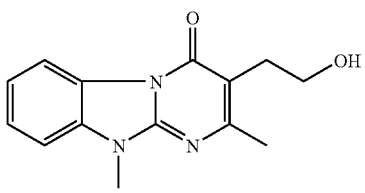

A mixture, of intermediate 22 (0.025 mol) and K$_2$CO$_3$ p.a. (0.03 mol) in DMF (70 ml) was stirred at 50° C. Methyliodide (0.03 mol) was added dropwise. The mixture was stirred at 50° C. for 4 hours and cooled. The solvent was evaporated. The residue was boiled in CH$_3$OH. The precipitate was filtered off and dried. The residue was purified by HPLC over silica gel (eluent: CH$_2$Cl$_2$/(CH$_3$OH/NH$_3$) 97/3). Two pure fractions were collected and their solvents were evaporated. Yielding: 2.08 g of 3-(2-hydroxyethyl)-2,10-dimethyl-pyrimido[1,2-a]benzimidazol-4(10H)-one (intermediate 23).

c) Preparation of Intermediate 24

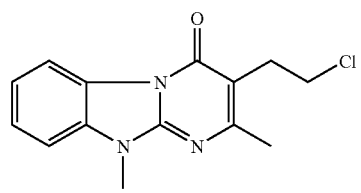

A mixture of intermediate 23 (0.02 mol) and SOCl$_2$ (0.06 mol) in CHCl$_3$ (50 ml) was stirred and refluxed for 4 hours and then cooled. H$_2$O was added. The mixture was alkalized with K$_2$CO$_3$ and separated into its layers. The aqueous layer was extracted with CH$_2$Cl$_2$. The combined organic layer was dried (MgSO$_4$), filtered and the solvent was evaporated. The residue was crystallized from CH$_3$CN. The precipitate was filtered off and dried. Yielding: 3.44 g of intermediate 24.

B. Preparation of the Final Compounds

EXAMPLE B1

Preparation of Compound 1

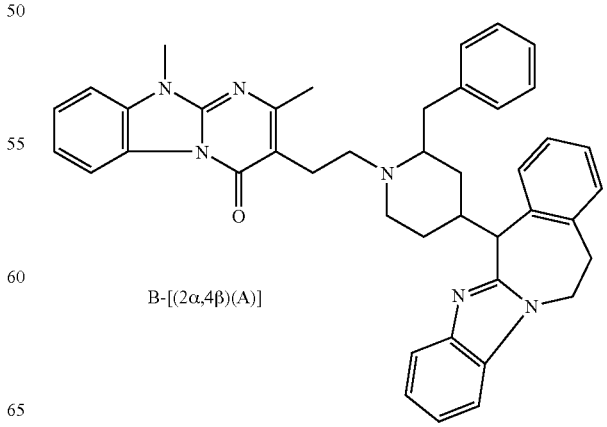

B-[(2α,4β)(A)]

and Preparation of Compound 2

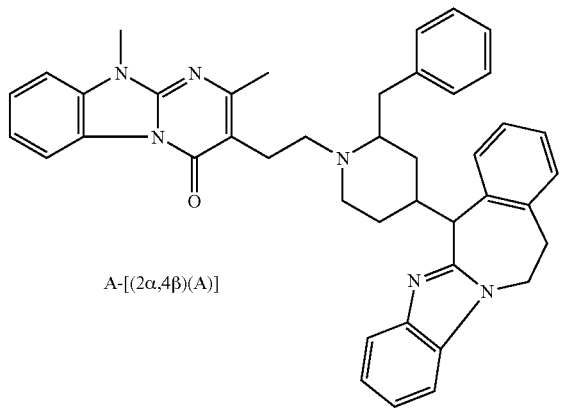

A-[(2α,4β)(A)]

A mixture of intermediate 24 (0.021 mol), intermediate 5 (0.015 mol), Na$_2$CO$_3$(0.021 mol) and KI (1 g) in MIBK (500 ml) was stirred and refluxed for 72 hours. The solvent was evaporated. The residue was partitioned between water and CH$_2$Cl$_2$. The layers were separated. The aqueous layer was re-extracted with CH$_2$Cl$_2$. The separated organic layer was dried (MgSO$_4$), filtered and the solvent evaporated. The residue was purified over silica gel on a glass filter (eluent: CH$_2$Cl$_2$/(CH$_3$OH/NH$_3$) 97/3 to 94/6). The desired fractions were collected and the solvent was evaporated. The residue was crystallized from CH$_3$CN, filtered off and dried. This fraction (6.95 g) was separated into its enantiomers over Chiralcel OD (eluent: hexane/(C$_2$H$_5$OH+0.04% Et$_3$N) 58/42). The pure fractions were collected and the solvent was evaporated. Fraction 1 was dissolved in 2-propanol/ethanol (95/5) and converted into the (E)-2-butenedioic acid salt (2:3). The precipitate was filtered off and dried. This fraction was dried. Yield: 2.2 g of (A)[(2α,4β)(A)] 3-[2-(4-(11,12-dihydro-6H-benzimidazo [2,1-b][3]benzazepin-6-yl)-2-(phenylmethyl)-1-piperidinyl]ethyl]-2,10-dimethyl-pyrimido[1,2-a]benzimidazol-4(10H)-one (compound 2) (45%). Fraction 2 was dissolved in 2-propanol/ethanol (95/5) and converted into the (E)-2-butenedioic acid salt (2:3). The precipitate was filtered off and dried. This fraction was dried. Yield: 2.1 g of (B)[(2α,4β)(A)]3-[2-(4-(11,12-dihydro-6H-benzimidazo [2,1-b][3]benzazepin-6-yl)-2-(phenylmethyl)-1-piperidinyl]ethyl]-2,10-dimethyl-pyrimido[1,2-a]benzimidazol-4(10H)-one (E)-2-butenedioate (2:3) hydrate (1:1) (compound 1) (43%).

EXAMPLE B2

Preparation of Compound 3

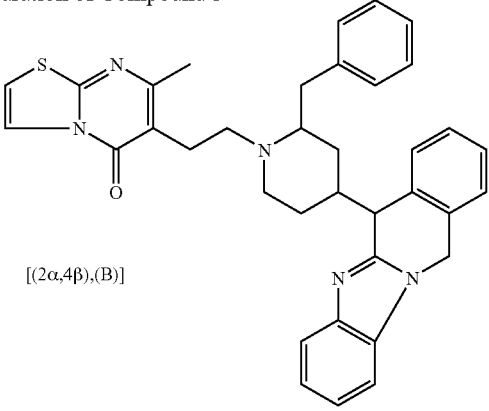

[(2α,4β),(B)]

and Preparation of Compound 4

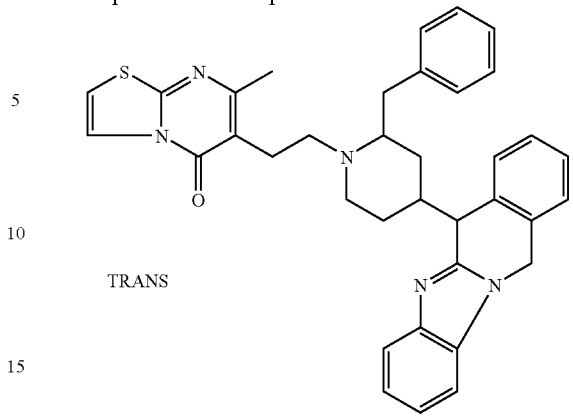

TRANS

Reaction under N$_2$ flow. A mixture of

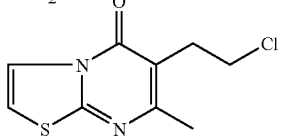

(0.0185 mol), intermediate 8 (0.0092 mol), NaHCO$_3$ (0.0185 mol) and KI (1 g) in MIK (200 ml) was stirred and refluxed for several hours. The solvent was evaporated. The residue was taken up in H$_2$O and CH$_2$Cl$_2$ and the mixture was separated into its layers. The aqueous layer was extracted with CH$_2$Cl$_2$. The combined organic layer was dried (MgSO$_4$), filtered and the solvent was evaporated. The residue was purified over silica gel on a glass filter (eluent: CH$_2$Cl$_2$/(CH$_3$OH/NH$_3$) 97/3). The pure fractions were collected and the solvent was evaporated. The residue was purified again by HPLC over RP 18 (eluent: [NH$_4$OAc (0.5% in H$_2$O)/CH$_3$CN 90/10]/CH$_3$CN 60/40). Two pure fractions were collected and their organic solvents were evaporated. The aqueous concentrates were extracted with CH$_2$Cl$_2$. The organic layers were separated, dried (MgSO$_4$), filtered and the solvent was evaporated. Yielding: Fraction 1 and 0.98 g of compound 4 (trans-isomer) (Fraction 2, 18%). Fraction 1 was crystallized from CH$_3$CN. The precipitate was filtered off and dried. Yielding: 0.8 g of compound 3 ([(2α,4β)(B)]-enantiomer)(15%).

EXAMPLE B3

Preparation of Compound 5

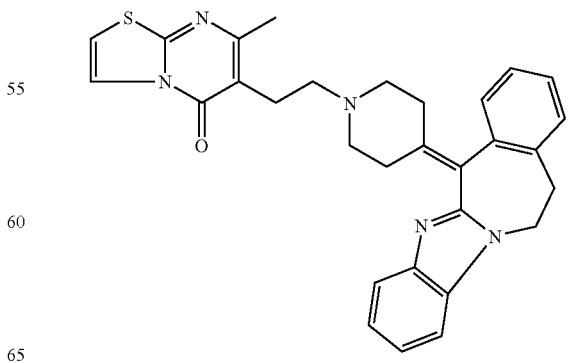

A mixture of

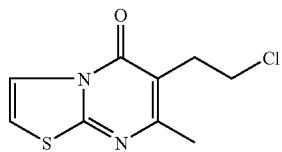

(0.01 mol), intermediate 13 (0.01 mol), Na₂CO₃ (0.025 mol) and KI (a catalytic amount) in, MIBK (200 ml) was stirred for 24 hours at 120° C. The reaction mixture was cooled and filtered over dicalite. The filtrate was evaporated. The residue was purified on a glass filter over silica gel (eluent: CH₂Cl₂/CH₃OH 96/4). The pure fractions were collected and the solvent was evaporated. The residue (3.9 g) was recrystallized from CH₃CN. The product was filtered off and dried. Yielding: 2.3 g of 6-[2-[4-(11,12-dihydro-6H-benzimidazo[2,1-b][3]benzazepin-6-ylidene)-1-piperidinyl]ethyl]-7-methyl-5H-thiazolo[3,2-a]pyrimidin-5-one (compound 5) (45.3%) (mp. 224.9° C.).

EXAMPLE B4

Preparation of Compound 6

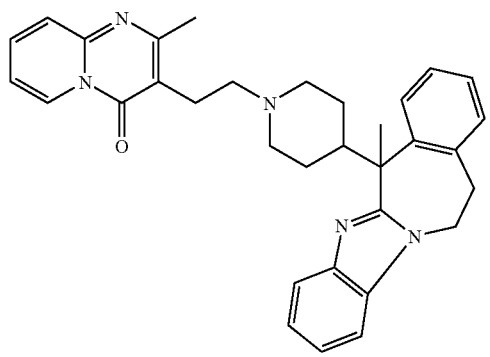

A mixture of intermediate 16 (0.0023 mol),

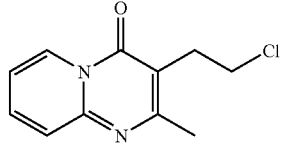

(0.0046 mol), Na₂CO₃ (0.0046 mol) and KI (0.0046 mol) in MIBK was stirred for 24 hours. The reaction mixture was hydrolyzed with water and extracted with CH₂Cl₂. The residue was purified by short open column chromatography over silica gel (eluent: CH₂Cl₂(CH₃OH/NH₃) 95/5), then by high-performance liquid chromatography over silica gel (eluent: CH₂Cl₂/(CH₃OH/NH₃) 97/3). The pure fractions were collected and the solvent was evaporated. Yielding: 0.250 g of compound 6 (23%) (mp.: 133.9° C.).

EXAMPLE B5

Preparation of Compound 7

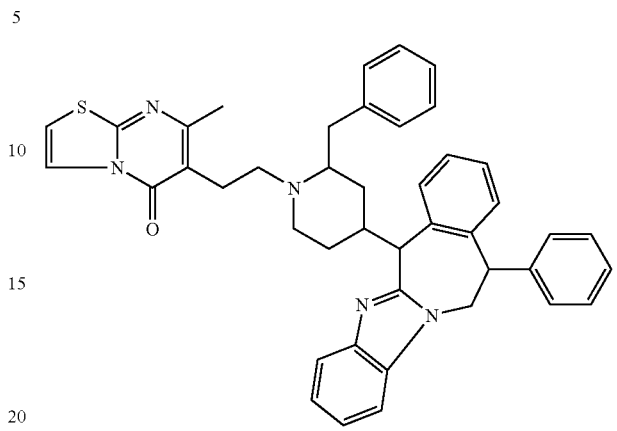

A mixture of intermediate 18 (0.0063 mol),

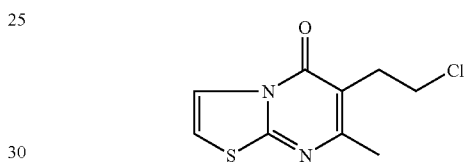

(0.0127 mol), Na₂CO₃ (0.0127 mol) and KI (0.0127 mol) in MIBK (200 ml) was stirred and refluxed overnight., H₂O was added and the mixture was extracted with, CH₂Cl₂. The residue was purified by high-performance liquid chromatography over silica gel (eluent: CH₂Cl₂/(CH₃OH/NH₃) 95/5). The pure fractions were collected and the solvent was evaporated. The residue was washed with CH₃CN, and dried. Yielding: 1 g of compound 7 (28%) (mp.: 213.2° C.).

EXAMPLE B6

Preparation of Compound 8

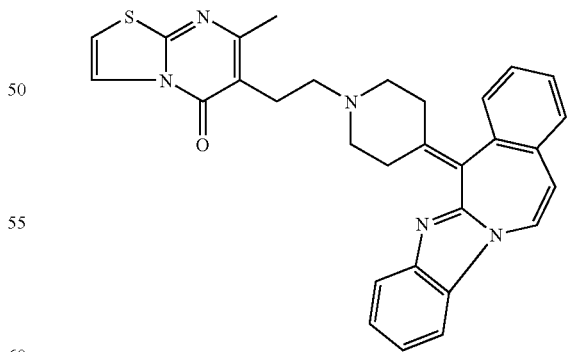

A mixture of 6-(2-chloroethyl)-7-methyl-5H-thiazolo[3,2-a]pyrimidin-5-one (0.012 mol), intermediate 13 (0.01 mol), Na₂CO₃ (0.01 mol) and KI (0.01 g) in MIBK (200 ml) was stirred and refluxed overnight. The reaction mixture was poured out into water. The layers were separated and the aqueous layer was re-extracted with 4-methyl-2-pentanone.

The organic layer was separated, dried (MgSO$_4$), filtered and evaporated. The residue was purified on a glass filter over silica gel (eluent: CH$_2$Cl$_2$/CH$_3$OH/(CH$_3$OH/NH$_3$) 90/10/1). The pure fractions were collected and the solvent was evaporated. The residue was crystallized from acetonitrile. The product was filtered off and dried. Yielding: 2.2 g of 6-[2-[4-(6H-benzimidazo[2,1-b][3]benzazepin-6-ylidene)-1-piperidinyl]ethyl]-7-methyl-5H-thiazolo[3,2-a]pyrimidin-5-one (compound 8) (43.5%) (mp.: 178.8° C.).

The compounds exemplified in the following tables were prepared in a manner analogous to one of the foregoing examples B1 to B6.

TABLE 1

| Comp. nr. | Ex. nr. | R$^1$ | R | X | Phys.data and stereochemistry |
|---|---|---|---|---|---|
| 9 | B1 | 2-benzyl | (1,2-dimethyl-4-oxo-pyrimido-benzimidazole, N-CH$_3$) | —CH$_2$—CH$_2$— | [(2α, 4α)(B)] |
| 10 | B1 | 2-benzyl | (2,3-dimethyl-4-oxo-pyrimido-benzothiazole) | —CH$_2$—CH$_2$— | [(2α, 4α)(B)] |
| 11 | B1 | 2-benzyl | (1,2,3-trimethyl-4-oxo-pyrimido-benzimidazole) | —CH$_2$—CH$_2$— | [(2α, 4α)(B)]; .H$_2$O(1:2) |
| 12 | B1 | 2-benzyl | (1-ethyl-2,3-dimethyl-4-oxo-pyrimido-benzimidazole) | —CH$_2$—CH$_2$— | [(2α, 4α)(B)] |
| 13 | B1 | 2-benzyl | (1,2,3-trimethyl-4-oxo-pyrimido-benzimidazole) | —CH$_2$—CH$_2$— | [(2α, 4β)(B)] |

TABLE 1-continued
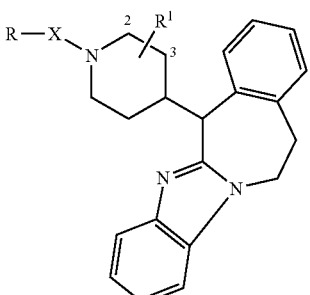
| Comp. nr. | Ex. nr. | R¹ | R | X | Phys.data and stereochemistry |
|---|---|---|---|---|---|
| 14 | B1 | H | 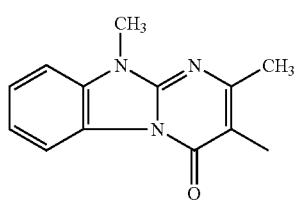 | —CH₂—CH₂— | |
| 15 | B1 | 2-benzyl | 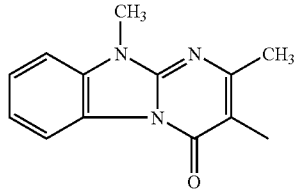 | —CH₂—CH₂— | [(2α, 4β)(A)]; E)-2-butenedioate (2:3) |
| 16 | B1 | 2-benzyl | 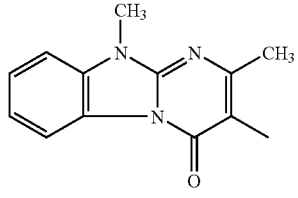 | —CH₂—CH₂— | [A(2α, 4α)(B)] |
| 17 | B1 | 2-benzyl |  | —CH₂—CH₂— | [B(2α, 4α)(B)] |
| 18 | B1 | 2- | 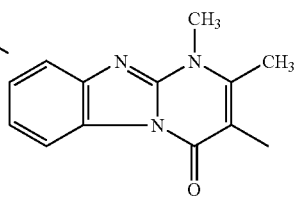 | —CH₂—CH₂— | |

TABLE 1-continued
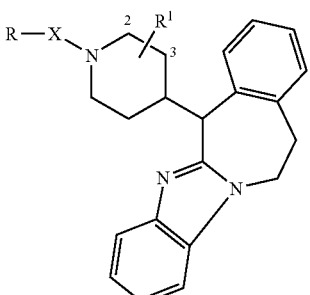
| Comp. nr. | Ex. nr. | R¹ | R | X | Phys.data and stereochemistry |
|---|---|---|---|---|---|
| 19 | B1 | 2-benzyl | 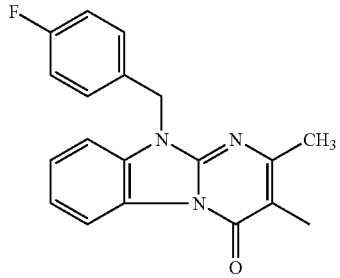 | —CH₂—CH₂— | [(2α, 4α)(B)] |
| 20 | B1 | 2-benzyl | 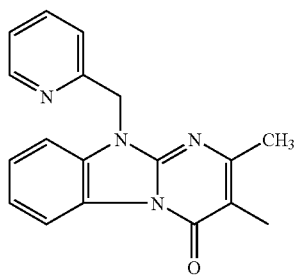 | —CH₂—CH₂— | [(2α, 4α)(B)] |
| 21 | B1 | 2-benzyl | 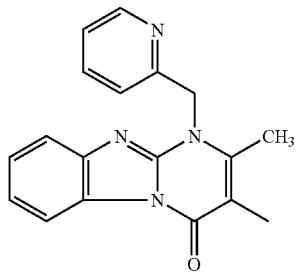 | —CH₂—CH₂— | [(2α, 4α)(B)] |
| 22 | B1 | 2-benzyl | 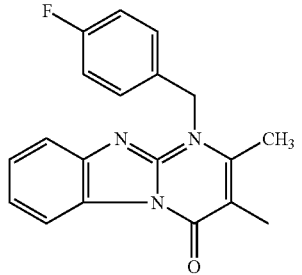 | —CH₂—CH₂— | [(2α, 4α)(B)] |

TABLE 1-continued

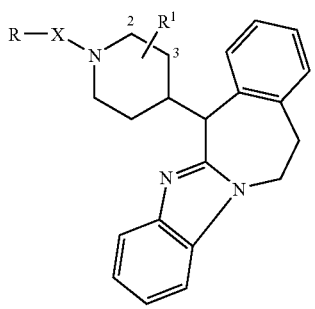

| Comp. nr. | Ex. nr. | R¹ | R | X | Phys.data and stereochemistry |
|---|---|---|---|---|---|
| 23 | B1 | 2-benzyl | H₃C—O—CH₂CH₂—[1-(benzimidazo-pyrimidinone with 2-CH₃, 3-CH₃)] | —CH₂—CH₂— | [(2α, 4α)(B)] |
| 24 | B1 | 2-benzyl | 3,5-dimethylbenzyl-[1-(benzimidazo-pyrimidinone with 2-CH₃, 3-CH₃)] | —CH₂—CH₂— | [(2α, 4α)(B)] |
| 25 | B1 | 2-benzyl | [7,8-dimethylbenzimidazo-pyrimidinone with 1-CH₃, 2-CH₃, 3-CH₃] | —CH₂—CH₂— | [(2α, 4α)(B)] |
| 26 | B1 | 2-benzyl | 3,5-dimethylbenzyl-[1-(benzimidazo-pyrimidinone with 2-CH₃, 3-CH₃)] | —CH₂—CH₂— | [(2α, 4α)(B)]; .H₂O(1:1) |

TABLE 1-continued
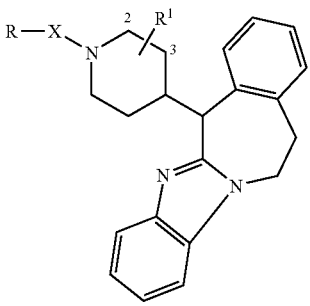
| Comp. nr. | Ex. nr. | R¹ | R | X | Phys.data and stereochemistry |
|---|---|---|---|---|---|
| 27 | B1 | 2-benzyl | 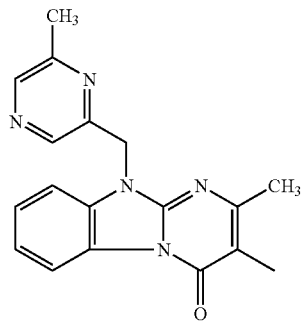 | —CH$_2$—CH$_2$— | [(2α, 4α)(B)] |
| 28 | B1 | 2-benzyl | 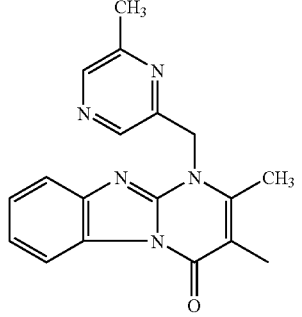 | —CH$_2$—CH$_2$— | [(2α, 4α)(B)] |
| 29 | B1 | 2-benzyl | 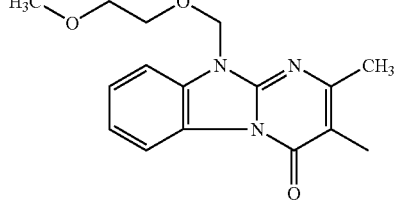 | —CH$_2$—CH$_2$— | [(2α, 4α)(B)] |
| 30 | B1 | 2-benzyl | 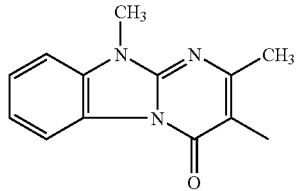 | —CH$_2$—CH$_2$— | [(2α, 4α)(A)] |

TABLE 1-continued
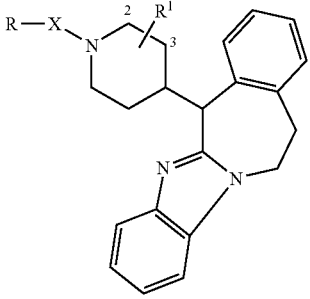
| Comp. nr. | Ex. nr. | R¹ | R | X | Phys.data and stereochemistry |
|---|---|---|---|---|---|
| 31 | B1 | 2-benzyl | 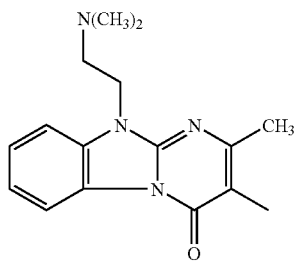 | —CH₂—CH₂— | [(2α, 4α)(B)] |
| 32 | B1 | 2-benzyl | 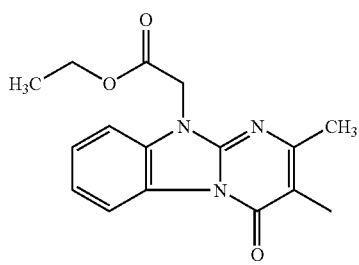 | —CH₂—CH₂— | [(2α, 4α)(B)] |
| 33 | B1 | 2-benzyl | 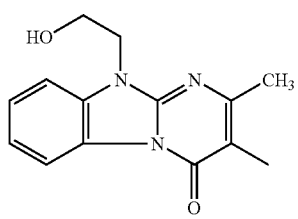 | —CH₂—CH₂— | [(2α, 4α)(B)] |
| 34 | B1 | 2-benzyl | 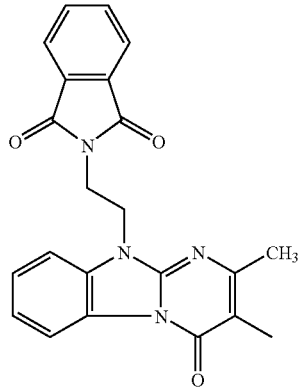 | —CH₂—CH₂— | [(2α, 4α)(B)]; .H₂O(1:1) |

TABLE 1-continued
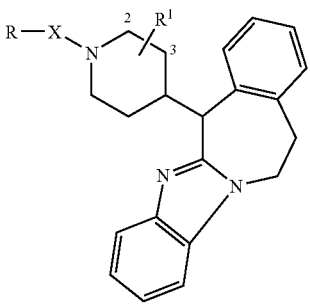
| Comp. nr. | Ex. nr. | R¹ | R | X | Phys.data and stereochemistry |
|---|---|---|---|---|---|
| 35 | B1 | 2-benzyl |  | —CH$_2$—CH$_2$— | [(2α, 4α)(B)]; .H$_2$O(1:1) |
| 36 | B1 | 2-benzyl | 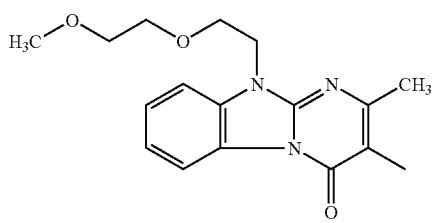 | —CH$_2$—CH$_2$— | [(2α, 4α)(B)]; .H$_2$O(1:1) |
| 37 | B1 | 2-benzyl | 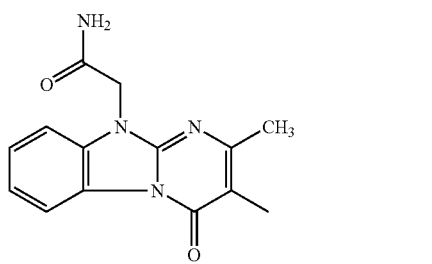 | —CH$_2$—CH$_2$— | [(2α, 4α)(B)] |
| 38 | B1 | 2-benzyl | 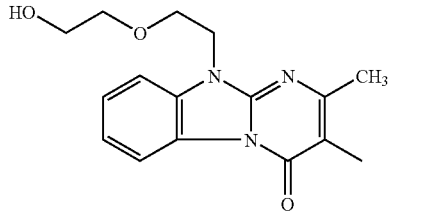 | —CH$_2$—CH$_2$— | [(2α, 4α)(B)]; .H$_2$O(1:1) |
| 39 | B1 | 2-benzyl | 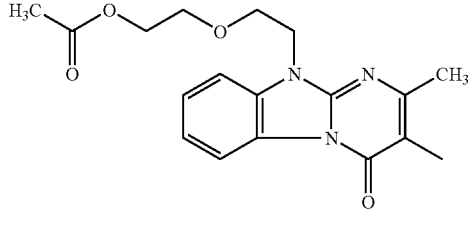 | —CH$_2$—CH$_2$— | [(2α, 4α)(B)]; .H$_2$O(1:1) |

TABLE 1-continued
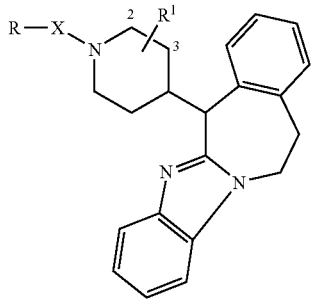
| Comp. nr. | Ex. nr. | R¹ | R | X | Phys.data and stereochemistry |
|---|---|---|---|---|---|
| 40 | B1 | 2-benzyl | 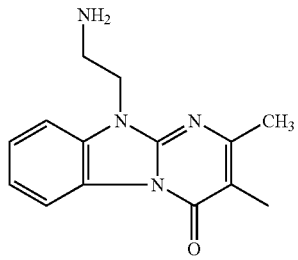 | —CH₂—CH₂— | [(2α, 4α)(B)] |
| 41 | B1 | 2-benzyl | 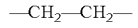 | —CH₂—CH₂— | [(2α, 4α)(B)] |
| 42 | B1 | 2-benzyl | 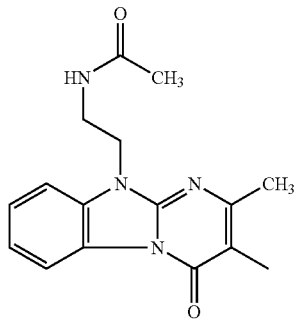 | —CH₂—CH₂— | [(2α, 4α)(B)] |
| 43 | B1 | 2-benzyl | 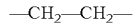 | (CH₂)₂—C(=O)— | [(2α, 4α)(A)] |

TABLE 1-continued

| Comp. nr. | Ex. nr. | R¹ | R | X | Phys.data and stereochemistry |
|---|---|---|---|---|---|
| 44 | B1 | 2-benzyl | (1,2,3-trimethyl-4-oxo-pyrimido-benzimidazole) | —CH₂—CH₂— | [A(2α, 4β)(A)] |
| 45 | B1 | 2-benzyl | (1,2,3-trimethyl-4-oxo-pyrimido-benzimidazole) | —CH₂—CH₂— | [B(2α, 4β)(A)] |
| 46 | B1 | 2-benzyl | (1,2,3-trimethyl-4-oxo-pyrimido-benzimidazole) | —CH₂—CH₂— | [A(2α, 4β)(B)]; Tri-fluoroacetate (1:1) |
| 47 | B1 | 2-benzyl | (1,2,3-trimethyl-4-oxo-pyrimido-benzimidazole) | —CH₂—CH₂— | [B(2α, 4β)(B)]; Tri-fluoroacetate (1:1) |
| 48 | B1 | 2-benzyl | (1,2,3-trimethyl-4-oxo-pyrimido-benzimidazole) | —CH₂—CH₂— | [(2α, 4β)(A)] |
| 49 | B1 | 2-benzyl | (1,2,3-trimethyl-4-oxo-pyrimido-benzimidazole) | —CH₂—CH₂— | [(2α, 4β)(A)]; (−)-[S(R*, R*)]-2,3-dihydroxy butanedioate (1:2) |

TABLE 1-continued
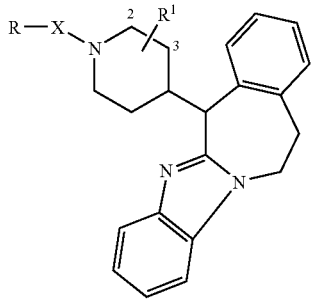
| Comp. nr. | Ex. nr. | R¹ | R | X | Phys.data and stereochemistry |
|---|---|---|---|---|---|
| 50 | B1 | 2-benzyl | 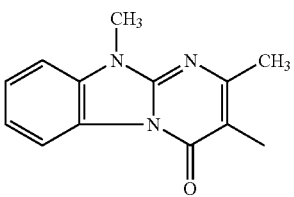 | —CH₂—CH₂— | [(2α, 4β)(A)]; .HCl(1:3).H₂O (1:2) |
| 51 | B1 | 2-benzyl | 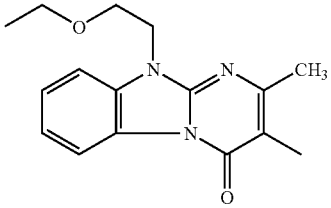 | —CH₂—CH₂—CH₂— | [(2α, 4β)(A)]; .H2O(1:2) |
| 52 | B1 | 2-benzyl | 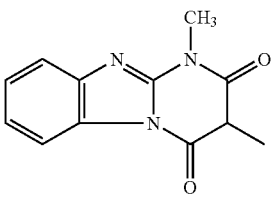 | —CH₂—CH₂— | [(2α, 4β)(A)] |
| 53 | B1 | 2-benzyl | 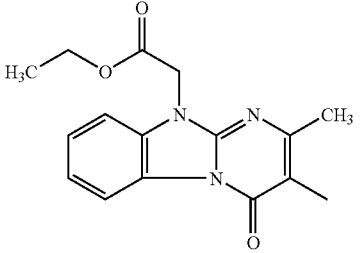 | —CH₂—CH₂— | [(2α, 4β)(A)] |
| 54 | B1 | 2-benzyl | 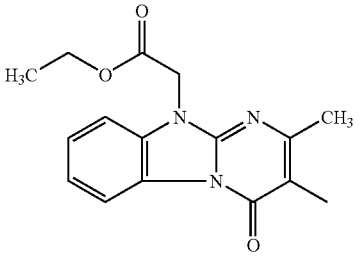 | —CH₂—CH₂— | [(2α, 4β)(A)]; (E)-2-butenedioate (1:1) |

TABLE 1-continued

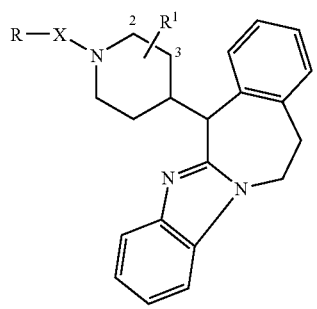

| Comp. nr. | Ex. nr. | R¹ | R | X | Phys.data and stereochemistry |
|---|---|---|---|---|---|
| 55 | B1 | 2-benzyl | (1,2,3-trimethyl-benzimidazo-pyrimidinone) | —CH₂—CH₂— | [(2α, 4β)(A)]; (E)-2-butenedioate (1:1).H₂O(1:2) |
| 2 | B1 | 2-benzyl | (1,2,3-trimethyl-benzimidazo-pyrimidinone) | —CH₂—CH₂— | [A(2α, 4β)(A)]; (E)-2-butenedioate (2:3).H₂O(1:1) |
| 1 | B1 | 2-benzyl | (1,2,3-trimethyl-benzimidazo-pyrimidinone) | —CH₂—CH₂— | [B(2α, 4β)(A)]; (E)-2-butenedioate (2:3).H₂O(1:1) |
| 56 | B1 | 2-benzyl | (2,3-dimethyl-thiazolo-pyrimidinone) | —CH₂—CH₂—CH₂— | [(2α, 4α)(B)] |
| 57 | B1 | 2-benzyl | (1,2,3-trimethyl-benzimidazo-pyrimidinone) | —CH₂—CH₂— | [A(2α, 4α)(A)] |
| 58 | B1 | 2-benzyl | (1,2,3-trimethyl-benzimidazo-pyrimidinone) | —CH₂—CH₂— | [B(2α, 4α)(A)] |

TABLE 1-continued
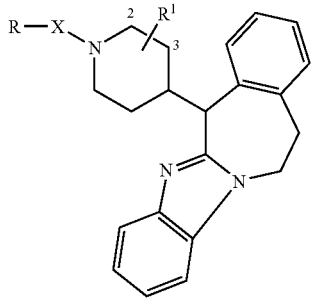
| Comp. nr. | Ex. nr. | R¹ | R | X | Phys.data and stereochemistry |
|---|---|---|---|---|---|
| 59 | B1 | 2-benzyl | 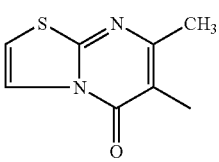 | 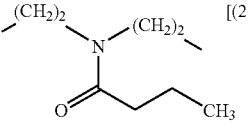 | [(2α, 4α)(A)] |
| 60 | B1 | 2-benzyl | 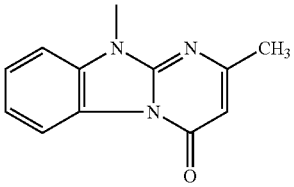 | —CH₂—CH₂— | [(2α, 4α)(B)] |
| 109 | B1 | 2-benzyl | 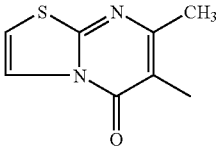 | —CH₂— | [(2α, 4α)(B)] |
| 152 | B1 | H | 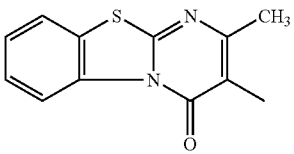 | —CH₂—CH₂— | |
| 153 | B1 | H | 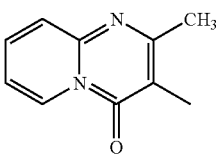 | —CH₂—CH₂—CH₂— | E)-2-Butenedioate (2:5) |

TABLE 2

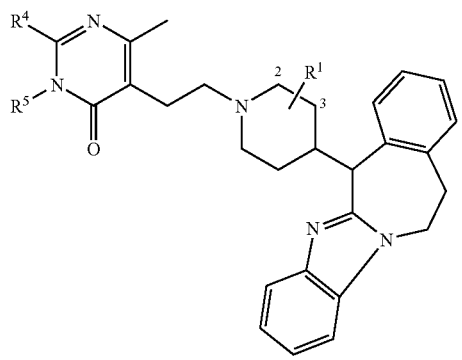

| Comp. nr. | Ex. nr. | R¹ | R⁵ R⁴ | Phys.data and stereochemistry |
|---|---|---|---|---|
| 61 | B2 | H | —CH=CH—S— | |
| 62 | B2 | H | —CH$_2$—CH$_2$—S— | |
| 63 | B2 | H | —CH$_2$—CH$_2$—CH$_2$—S— | |
| 64 | B2 | H | —CH=CH—CH=CH— | |
| 65 | B2 | H | —CH$_2$—C(CH$_3$)=N—N(CH$_3$)— | |
| 66 | B2 | H | —C(CH$_3$)=N—N(CH$_3$)— | |
| 67 | B2 | H | —CH=CH—N(CH$_3$)— | |
| 68 | B2 | H | —O—C(CH$_3$)=CH— | |
| 69 | B2 | H | —CH=C(CH$_3$)—N(CH$_3$)— | |
| 70 | B2 | H | —CH=C(CH$_3$)—CH=CH— | |
| 71 | B2 | H | —C(CH$_3$)=CH—S— | |
| 72 | B2 | H | —CH=CH—CH=C(CH$_3$)— | |
| 73 | B2 | 2-benzyl | —CH=CH—S— | [(2α, 4β)(B)] |
| 74 | B2 | 2-benzyl | —CH=CH—S— | [(2α, 4α)(A)] |
| 75 | B2 | 2-benzyl | —CH=CH—S— | [(2α, 4α)(B)] |
| 76 | B2 | 2-benzyl | —CH=CH—S— | [(2α, 4β)(A)]; .(E)-2-butenedioate (1:2).ethanolate (1:1) |
| 77 | B2 | 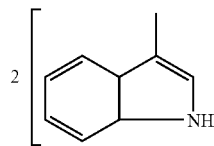 | —CH=CH—S— | [(2α, 4α)(A)] |
| 78 | B2 | 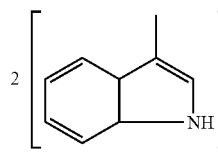 | —CH=CH—S— | [(2α, 4β)(B)] |
| 79 | B2 | 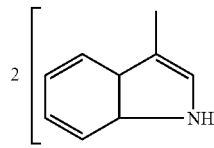 | —CH=CH—S— | [(2α, 4α)(B)] |
| 80 | B2 | 2-benzyl | —CH=CH—CH=CH | [(2α, 4α)(B)] |
| 81 | B2 | 2-benzyl | —CH=CH—CH=CH— | [(2α, 4β)(A)] |
| 82 | B2 | 2-benzyl | —CH=CH—CH=CH— | [(2α, 4β)(B)] |
| 83 | B2 | 2-naphthylmethyl | —CH=CH—S— | [(2α, 4β)(A)] |
| 84 | B2 | 2-naphthylmethyl | —CH=CH—S— | [(2α, 4β)(B)] |

TABLE 2-continued

| Comp. nr. | Ex. nr. | R¹ | R⁵  R⁴ | Phys.data and stereochemistry |
|---|---|---|---|---|
| 85 | B2 | 2-naphthylmethyl | —CH=CH—S— | [(2α, 4α)(B)] |
| 86 | B2 | 2-naphthylmethyl | —CH=CH—S— | [(2α, 4α)(A)]; .H₂O(1:1) .ethanolate(1:1) |
| 87 | B2 | 3-methyl | —CH=CH—S— | A-trans |
| 88 | B2 | 3-methyl | —CH=CH—S— | B-trans |
| 89 | B2 | 3-methyl | —CH=CH—CH=CH— | [(3α, 4β)(B)] |
| 90 | B2 | 3-(4-fluorobenzyl) | —CH=CH—S— | [(2α, 4β)(A)] |
| 91 | B2 | 3-(4-fluorobenzyl) | —CH=CH—S— | [(2α, 4β)(A)] |
| 92 | B2 | 3-(4-fluorobenzyl) | —CH=CH—S— | [(2α, 4α)(A)] |
| 93 | B2 | 3-(4-fluorobenzyl) | —CH=CH—S— | [(2α, 4α)(B)] |
| 94 | B2 | 3-methyl | —CH=CH—CH=CH— | [(3α, 4β)(A)] |
| 95 | B2 | 2-benzyl | —CH=C(CH₃)—N(CH₃)— | [(2α, 4α)(B)] |
| 96 | B2 | 2-benzyl | —CH=CH—N(CH₃)— | [(2α, 4α)(B)] |
| 97 | B2 | 2-benzyl | —CH=CH—CH=C(CH₃)— | [(2α, 4α)(B)] |
| 98 | B2 | 2-benzyl | —CH₂—CH₂—S— | [(2α, 4α)(B)] |
| 99 | B2 | 2-benzyl | —CH₂—C(CH₃)=N—N(CH₃)— | [(2α, 4α)(B)] |
| 100 | B2 | 2-benzyl | —CH=C(CH₃)—CH=CH— | [(2α, 4α)(B)] |
| 101 | B2 | 2-benzyl | —C(CH₃)=CH—C(CH₃)=CH— | [(2α, 4α)(B)] |
| 102 | B2 | 2-benzyl | —CH=C(Cl)—CH=C(Cl)— | [(2α, 4α)(B)] |
| 103 | B2 | 2-benzyl | —CH=C(CF₃)—CH=C(Cl)— | [(2α, 4α)(B)] |
| 104 | B2 | 4-methyl | —CH=CH—S— | |
| 105 | B2 | 2-(cyclohexylethyl) | —CH=CH—CH=CH— | |
| 106 | B2 | 2-benzyl | —CH=CH—S— | [A(2α, 4α)(B)] |
| 107 | B2 | 2-benzyl | —CH=CH—S— | [B(2α, 4α)(B)] |
| 108 | B2 | 2-(cyclohexylethyl) | —CH=CH—S— | |

TABLE 3

| Comp. nr. | Ex. nr. | R² | R⁵―R⁴ | Phys.data and stereochemistry |
|---|---|---|---|---|
| 6 | B4 | a-methyl | —CH=CH—CH=CH— | hydrate (1:1) |
| 110 | B4 | a-methyl | —CH=CH—S— | |
| 111 | B4 | a-benzyl | —CH=CH—CH=CH— | |
| 112 | B5 | b-benzyl | —CH=CH—CH=CH— | |
| 7 | B5 | b-benzyl | —CH=CH—S— | |
| 113 | B4 | a-phenyl | —CH=CH—S— | |

TABLE 4

| Comp. nr. | Ex. nr. | R⁵―R⁴ | A―B | C―D | Phys.data and stereochemistry |
|---|---|---|---|---|---|
| 114 | B1 | —CH=CH—CH=CH— | —CH=CH—S— | —CH=CH—CH=CH— | H₂O(1:1) (E)-2-butenedioate(1:1) |
| 115 | B1 | —CH=CH—S— | —CH=CH—S— | —CH=CH—CH=CH— | H₂O(2:1) (E)-2-butenedioate(2:3) |
| 116 | B1 | —CH=CH—CH=CH— | —CH=CH—CH=CH— | —N=CH—CH=CH— | |
| 117 | B1 | —CH=CH—S— | —CH=CH—CH=CH— | —N=CH—CH=CH— | |
| 118 | B1 | —CH=CH—S— | —CH=CH—N(CH₃)— | —N=CH—CH=CH— | |

TABLE 5

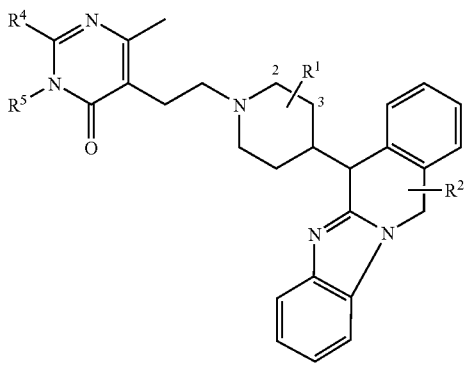

| Comp. nr. | Ex. nr. | R¹ | R² | R⁵ R⁴ | Phys.data and stereochemistry |
|---|---|---|---|---|---|
| 119 | B2 | 2-benzyl | H | —CH=CH—S— | cis |
| 3 | B2 | 2-benzyl | H | —CH=CH—S— | [(2α, 4β)(B)] |
| 4 | B2 | 2-benzyl | H | —CH=CH—S— | trans |
| 120 | B2 | 2-benzyl | H | —CH=CH—CH=CH— | [(2α, 4β)(B)] |
| 121 | B2 | 2-benzyl | H | —CH=CH—CH=CH— | [(2α, 4β)(A)] |
| 122 | B2 | H | H | —CH₂—CH₂—CH₂—CH₂— | |
| 123 | B2 | H | H | —CH₂—CH₂—CH₂—S— | |
| 124 | B2 | H | H | —CH=CH—CH=CH— | |
| 125 | B2 | H | H | —CH₂—CH₂—S— | |
| 126 | B2 | H | H | —C(CH₃)=CH—S— | |
| 127 | B2 | H | H | —CH=C(CH₃)—CH=CH— | |
| 128 | B2 | H | H | —CH=CH—CH=C(CH₃)— | |
| 129 | B2 | H | H | —CH₂—C(CH₃)=N—N(CH₃)— | |
| 130 | B2 | H | H | —CH=CH—N(CH₃)— | |
| 131 | B2 | H | H | —CH=C(CH₃)—N(CH₃)— | |
| 132 | B2 | H | H | —O—C(CH₃)=CH— | (E)-2-butenedioate (1:2) |
| 133 | B2 | H | H | —C(CH₃)=N—N(CH₃)— | .H₂O(1:1) |
| 134 | B2 | 2-benzyl | H | —CH=CH—CH=CH— | [(2α, 4α)(B)] |
| 135 | B2 | 2-benzyl | H | —CH=CH—CH=CH— | [(2α, 4α)(A)] |
| 136 | B2 | H | H | —CH=CH—S— | .ethanedioate(2:5) .H₂O(2:1) |

TABLE 6

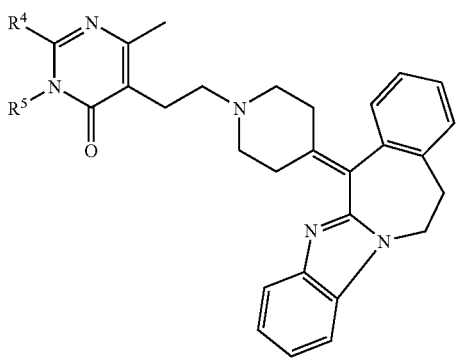

| Comp. nr. | Ex. nr. | R⁵ R⁴ | Phys.data and stereochemistry |
|---|---|---|---|
| 5 | B3 | —CH=CH—S— | |
| 137 | B3 | —CH₂—CH₂—S— | |
| 138 | B3 | —CH₂—CH₂—CH₂—S— | |
| 139 | B3 | —CH=CH—CH=CH— | |

TABLE 7

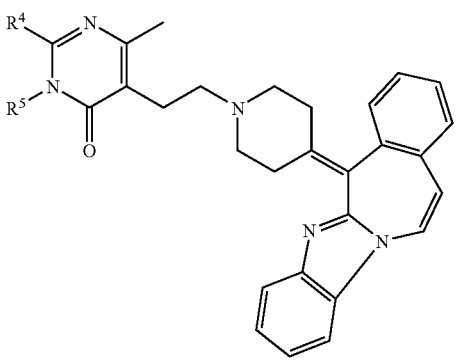

| Comp. nr. | Ex. nr. | R⁵ R⁴ | Phys.data and stereochemistry |
|---|---|---|---|
| 140 | B6 | —CH=CH—CH=CH— | |
| 141 | B6 | —CH₂—CH₂—CH₂—S— | |
| 8 | B6 | —CH=CH—S— | |
| 142 | B6 | —CH₂—CH₂—S— | |

TABLE 8

[Structure: pyrimidinone with R4, R5 substituents, linked via ethyl to piperidine (with R1) bearing benzimidazole-fused ring system with Y linker]

| Comp. nr. | Ex. nr. | Y | R¹ | R⁴ | R⁵ | Phys.data and stereochemistry |
|---|---|---|---|---|---|---|
| 143 | B2 | —CH₂—CH₂— | H | (pyridin-2-yl)-CH₂-NH- | —CH₃ | |
| 144 | B1 | —CH₂—CH₂— | H | H₃C-O-CH₂CH₂-NH- | —CH₃ | |
| 145 | B1 | —CH₂—CH₂— | H | H₃C-CH₂CH₂-NH- | —CH₃ | .H₂O(1:1) |
| 146 | B1 | —CH₂—CH₂— | H | H₃C-NH- | —CH₃ | |
| 150 | B1 | —CH₂—CH₂— | 2-benzyl | —NH₂ | —CH₃ | [(2α, 4α)(B)] |
| 147 | B2 | —CH₂— | H | —NH₂ | —CH₃ | (Z)-2-Butenedioate (1:3).H₂O(1:1) |
| 148 | B2 | —CH₂— | H | H₃C-NH-C(O)-NH- | —CH₃ | |
| 149 | B2 | —CH₂— | H | Ph-C(O)-NH- | —CH₃ | |
| 151 | B2 | —CH₂— | H | H₃C-CH₂-NH- | —CH₃ | .HCl(1:3) .H₂O(1:2) .2-propanolate. (2:1) |

C. Pharmacological Examples

C.1. In Vivo Pharmacology

Closed Head Injury (CHI) Model

A clinically relevant rat model for traumatic brain injury was used to test the compounds according to the invention. This model mimics several clinical features of traumatic brain injury, such as increased ICP, decreased cerebral perfusion pressure, morphologic alterations including diffuse axonal injury, neuronal necrosis and contusion, impairment of autoregulation of cerebral blood flow and reduction of brain oxygenation and was applied for screening drugs with ICP-lowering effects. Trauma was induced in intubated, isoflurane anesthetized (1.5% isoflurane in a mixture of 30% O₂ and 70% N₂O) Sprague-Dawley rats (380-400 g) stereotaxically positioned on a table mounted on 4 springs. A 400 g steel cylinder, protected with a 9 mm diameter silicon disc, was dropped on the unprotected skull from a height of either 70 cm or 50 cm (respectively 'severe' and 'moderate' head injury). The impact area was centered between bregma and lamda. ICP was recorded using a Codman microsensor probe inserted in the parietal cortex. In both severe and moderate head injuries the ICP increased immediately after trauma and remained elevated for several days. The severe head injury mode was used for the evaluation of pharmacological effects immediately after trauma (screening procedure). When survival and recovery from anesthesia was envisaged, the moderate head injury mode was applied. In pharmacological studies, animals with a pathological ICP between 12.5 and 35 mm Hg were included. The changes in ICP, mean arterial blood pressure (MABP) and cerebral perfusion pressure CPP (=MABP-CPP) were expressed as percentage of the initial value at onset of the treatment. Screening procedure: On a weekly base, 4 treated groups of 3 rats were compared with 3 saline treated animals. Since conventional statistical methods require a larger amount of animals, a sequential procedure was used. Sequential methods operate in different stages. At each stage, a group of animals was selected as homogeneous as possible. Animals were randomly allocated to either drugs or saline. The procedure allowed to make the decision of rejecting the drug, accepting the drug as active or to continue with a new group of animals in a next stage. Given the biological relevant level of activity that must be detected, the expected fraction of false positive and negative results was known and fixed. A sequential two-sample grouped rank test was used. A three stage sequential design with a relatively small number of animals at each stage showed to be optimal. Despite the variability in the individual data, the procedure consistently accepted reference treatments such as mannitol as active, while controls were rejected. Clinically relevant i.v. doses of mannitol (3 g over 45 min) consistently reduced the ICP (mean reduction about 20%).

TABLE 1

Results of the screening procedure.

| Treatment [1] | Delta % [2] | Decision [3] |
|---|---|---|
| Compound 9 | −12.4 | active |
| Compound 15 | −23.3 | active |
| Compound 17 | −8.9 | active |
| Compound 30 | −9.3 | active |
| Compound 32 | −13.9 | active |
| Compound 44 | −14.8 | active |
| Compound 45 | −13.1 | active |
| Compound 47 | −12.0 | active |
| CD10% | 5.1 | not active |
| CD10% + 3H2T | 10.0 | not active |
| CD20% | 19.1 | not active |
| CD20% + HCl | 2.4 | not active |
| Mannitol[1] | −21.7 | active |
| Mannitol[2] | −22.1 | active |
| Mannitol[3] | −13.0 | active |
| Mannitol[4] | −19.3 | active |
| Mannitol[5] | −19.9 | active |

(1) Experimental compounds administered as a bolus of 1 mg/kg given in 1 min, followed by an infusion of 0.5 mg/kg/min for 44 min; solvents administered as a 0.4 ml bolus in 1 min followed by an infusion of 0.2 ml/min for 44 min; mannitol given as an infusion of 67 mg/kg/min for 45 min.
(2) Delta %: average change of the relative ICP from baseline over the treatment period.
(3) Decision: based upon sequential statistical evaluation.
CD = hydroxypropyl-β-cyclodextrin solvent
H2T = tartaric acid solvent
Mannitol[1-5]: Mannitol was evaluated 5 times in separate tests (positive controls). The result of each test is mentioned.

Further Studies

Table 2 shows the changes in some relevant physiological variables recorded during treatment after severe CHI in rats. Treatment was started at 20 min after severe head injury and involved administering a dose of 0.5 mg/kg/min during 10 minutes, followed by 0.1 mg/kg/min during 50 min.

TABLE 2

Changes in relevant physiological variables during treatment after severe CHI in rats.

| | Solvent (n = 10) | Compound 2 (n = 10) | Compound 1 (n = 10) | Racemate (comp. 1 and comp. 2) (n = 10) |
|---|---|---|---|---|
| ICP (%) | 1.6 (−9.4; 11.1) | −15.3 (−20.0; −9.5)* | −15.4 (−22.6; −11.5)* | −19.1 (−24.9; −10.8)* |
| MABP (%) | −1.2 (−2.7; 3.7) | 18.8 (−2.0; 31.0)* | −3.6 (−11.9; −1.5) | 0.6 (−5.1; 8.5) |
| CPP (%) | −1.3 (−8.0; 5.8) | 24.2 (0.9; 43.6)* | −1.9 (−8.9; 0.4) | 7.5 (−2.4; 15.5) |
| ETCO$_2$ (%) | 8.0 (−1.2; 12.9) | −4.4 (−8.9; 2.3)* | 2.2 (−0.8; 8.4) | 2.4 (−7.8; 3.8) |
| Heart rate(%) | −2.7 (−5.4; 3.9) | −9.6 (−21.8; 0.7) | −4.1 (−11.4; 1.9) | 5.6 (−11.7; 0.4) |
| Resp. rate(%) | 3.6 (−4.3; 11.8) | 6.6 (−1.3; 14.6) | 5.3 (−3.3; 13.6) | 9.6 (3.0; 14.8) |

Average change over the entire treatment period, expressed as % change of initial value.
Values are medians (95% C.I.).
* = Significantly different from solvent group (p < 0.05, Dunnett's test)
Solvent: 10% hydroxypropyl-beta-cyclodextrine, tartaric acid, NaOH and mannitol in pyrogen free water; pH = 4; osmolarity 312-314 mOsm/ kg; compound concentration 2 mg/ml
Compound: pyrimido[1,2-α]benzimidazol-4(10H)-one, 3-[2-[4-(11,12-dihydro-6H-benzimidazo[2,1-b][3]benzazepin-6-yl)-2-(phenylmethyl)-1-piperidinyl]ethyl]-2,10-dimethyl (E)-2-butenedioate (2:3) hydrate (1:1)
Compound 2: (A)[(2α, 4β)(A)]
Compound 1: (B)[(2α, 4β)(A)]
Racemate (comp. 1 and comp. 2): (2α, 4β)(A), i.e. the racemic mixture of Compounds I and II
ICP: Intracranial pressure
MABP: Mean arterial blood pressure
CPP: Cerebral perfusion pressure
ETCO$_2$: End tidal CO$_2$ The significant effect of compound 2 on MABP is much less pronounced when the compound is given at a continuous infusion of 0.1 mg/kg.min. In this case a blood pressure peak is not present and increases in MABP larger than 20% are not observed (median MABP increase at the end of the infusion is 9%, n=6). The maximal reduction of ICP at this dose is comparable to the one observed when the infusion is preceded by the 'loading dose' of 5 mg/kg over 10 min, but the time required to obtain this effect is longer (median: 30 min).

Dose Response for Compound 1

Results of a blinded, completely randomized study of the effect of a 10 min infusion of Compound 1 at different doses (0.125, 0.25, 0.5, 1 and 2 mg/kg/min) in the rat CHI model indicate that during treatment Compound 1 invokes a sustained dose-dependent decrease of ICP (FIG. 1). Starting at 1 mg/kg/min Compound 1 yields a statistically significant larger reduction in ICP than in the solvent-treated group. In the 10 min period following the infusion a highly significant dose-dependent effect on ICP remains present (FIG. 2).

Effects of Compound 2, Compound 1 and Racemate (Comp. 1 and Comp. 2) on Brain Hemoglobin Concentration and Oxygenation.

Near-infrared spectroscopy (NIRS) of the rat brain 'in vivo' allows to quantify non-invasively saturation of brain haemoglobin with oxygen (HbSat) and total brain haemoglobin concentration ([HbTot]). The latter is a measure for cerebral blood volume (CBV). Changes in the redox state of the mitochondrial enzyme cytochrome oxidase (CytOx), an indicator for tissue oxygenation, can also be monitored.

All compounds 2, 1 and the racemate (Comp. 1 and Comp. 2) do not have a significant effect on [HbTot] when given 24 h after moderate head injury at a i.v. dose of 0.5 mg/kg.min during 10 min, followed by 0.1 mg/kg.min during 45 min. Only compound 2 induces a small but statistically significant reduction of HbSat. HbSat is not affected by compound 1 and the racemate (Comp. 1 and Comp. 2). At the applied dose all compounds do not have an effect on the redox state of CytOx. These results indicate that in the applied experimental conditions a vasoconstrictive effect on cerebral blood vessels, if present, is limited and tissue oxygenation is not jeopardised.

Influence of Anaesthesia on the Effects of Compound 2

The effects of treatment with Compound 2 (i.v. infusion at a dose of 0.1 mg/kg.min during 30 min) at 24 h after moderate trauma were studied using different anesthetics (isoflurane, chloralhydrate, pentobarbital). When chloralhydrate (400 mg/kg i.p) is used as anesthetic, ICP decreases to 75% of initial value and MABP gradually increases to 110% of initial value (medians, n=6). These effects are comparable with those observed under isoflurane anesthesia. When pentobarbital (60 mg/kg i.p.) is used, Compound 2 induces a significant gradual increase in MABP up to 141% of initial value at the end of the infusion, whereas ICP decreases to 64% of initial value (medians, n=6). These results indicate that the same pattern of effects on ICP and MABP are observed under various types of anesthesia. The fact that the compound reduces the ICP significantly under pentobarbital anesthesia is important, as barbiturates are often applied in traumatic brain injury patients. Barbiturates also reduce the ICP and an important additional effect can be obtained with the compound.

The Effect of Repeated Application of Compound 1 and of Mannitol on Elevated ICP in Traumatized Rats.

Compound 1 was given 2 times with intermittent periods of 20 min at a i.v. dose of 1 mg/kg/min during 10 min, starting a first time 20 min after induction of severe head injury.

Mannitol was given i.v. in the same time windows as Compound 1 at a dose of 0.125 g/kg/min. The control animals received the solvent (containing 10% HP-β-CD, pH 4) only.

Infusion with Compound 1 results in rapid reduction of ICP (FIG. 3). This effect is amplified after termination of each, infusion period. Blood pressure drops during Compound 1 treatment but is restored again after this episode. This is in contrast with mannitol, that induces a lowering of ICP and an increase in blood pressure during each infusion followed by a decrease in blood pressure after termination of each treatment.

Only in the Compound 1—treated animals a clear dissociation between the changes in blood pressure and ICP can be observed. In contrast, the mannitol treated animals exhibit more or less parallel changes in blood pressure and intracranial pressure. This indicates that the pharmacological effect of Compound 1 is different from that of mannitol.

Effect of Compound 1 on Cold Lesion-Induced Rise of ICP in Rabbits

Cryo-lesions were induced in adult rabbits to obtain a pathological ICP that is caused by tissue oedema. A 8 mm stainless steel rod was placed at predetermined coordinates on the exposed skull of deeply anaesthetised rabbits and cooled for min with liquid nitrogen. One day later the animals were re-anaesthetised and ICP and blood pressure continuously recorded as described for the rat. After a stabilisation period of 15 min, Compound 1 was infused for 10 min at a dose of 2 mg/kg/min. Solvent (preclinical formulation containing 10% HP-β-CD, pH 4) was given for 10 min at a rate of 2 m/min.

During infusion of the Compound 1, the blood pressure, drops and although there, is no immediate decrease in ICP, the ICP rise that is observed in the solvent-treated animals tends to be antagonised (FIG. 4). When drug infusion is terminated, blood pressure comes back to the initial value and a significant ICP reduction is seen that persists during the entire recording period. These results indicate that the compound reduces the ICP also in non-rodent species and in pathologic conditions different from closed head injury.

The Effect of Compound 1 and on ICP in Non-Traumatized Animals.

Rats

The effect of Compound 2, Compound 1 and Racemate (comp. 1 and comp. 2) on ICP, MABP and CPP was tested in anaesthetised non-traumatised rats. The compounds were administered i.v. and the same dose was given as in traumatized rats (0.5 mg/kg/min during 10 minutes, followed by 0.1 mg/kg/min during 50 min). The results, were comparable with those obtained in the traumatized animals.

Primates

The effect of Compound 1 on ICP was tested in a limited number of anaesthetised non-traumatised Rhesus monkeys with a i.v. infusion of a dose of 2.5 and 5 mg/kg over 2.5 and 5 min respectively (n=2/condition). The pattern of ICP and blood pressure changes during and after infusion of the compound resembles the pattern of changes observed in cryo-lesioned rabbits.

The results obtained in traumatized animals, animals with cold lesion, and non-traumatized animals indicate that the compounds are active in various conditions, even in normal conditions. Their field of application probably includes various pathological conditions in which intracranial hypertension is present.

Compounds according to the invention may therefore also be used to reduce a (normal) ICP, and even prophilacticly to prevent a rise in ICP, e.g. after acquired brain injury.

The invention claimed is:

1. A compound according to Formula (I),

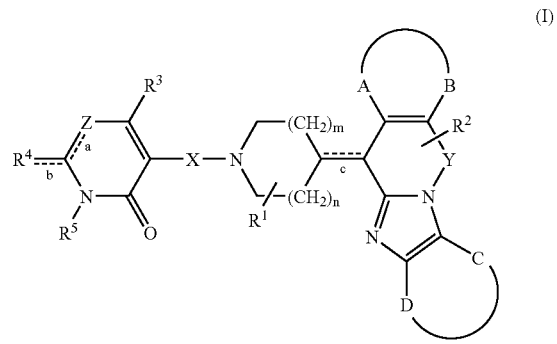

the pharmaceutically acceptable acid or base addition salts thereof, the stereochemically isomeric forms thereof and the N-oxide form thereof, wherein:

m is 1;

n is 1;

a, b, c independently are a single or a double bond;

X is a covalent bond or a bivalent $C_{1-6}$alkanediyl radical wherein one or more —$CH_2$— groups may be optionally replaced with —O—, —S—, —C(=O)— or $NR^7$—; wherein:
  $R^7$ is selected from the group consisting of hydrogen, alkyl, Ar, Ar-alkyl, Het, Het-alkyl, hydroxyalkyl, alkyloxy, alkyloxyalkyl, alkyloxyalkyloxyalkyl, aminoalkyl, mono- or dialkylaminoalkyl, formyl, alkylcarbonylaminoalkyl, alkylcarbonyloxyalkyl, alkyloxycarbonyl, alkyloxycarbonylalkyl, alkylaminocarbonyl, alkylaminocarbonylalkyl, hydroxyalkyloxyalkyl, aminocarbonyl, aminocarbonylalkyl, alkyloxycarbonyl, alkylcarbonyl and alkylcarbonyloxyalkyloxyalkyl;
Y is —$CH_2$—$CH_2$—;
Z is N, in which case a is a double bond and b is a single bond; or is N—$R^7$ in which case a is a single bond and $R^7$ is defined as above;
$R^1$, $R^2$ independently are selected from the group consisting of hydrogen, hydroxy, alkyl, alkyloxy, Ar, Ar-alkyl, di(Ar—)alkyl, Het and Het-alkyl;
-A-B— independently is selected from the group consisting of a bivalent radical of formula $$-E-CR^8=CR^8- \quad (a\text{-}1);$$

$$-CR^8=CR^8-E- \quad (a\text{-}2);$$

and $$-CR^8=CR^8-CR^8=CR^8- \quad (a\text{-}3);$$

wherein:
$R^8$ each independently is selected from the group consisting of hydrogen, halo, hydroxy, alkyl or alkyloxy;
E is selected from the group consisting of a bivalent radical of formula —O—, —S— and —$NR^7$— wherein $R^7$ is defined as above;
—C-D- independently is selected from the group consisting of a bivalent radical of formula $$-CR^8=CR^8-CR^8=CR^8- \quad (b\text{-}1);$$

$$-N=CR^8-CR^8=CR^8- \quad (b\text{-}2);$$

$$-CR^8=N-CR^8=CR^8- \quad (b3);$$

$$-CR^8=CR^8-N=CR^8- \quad (b\text{-}4);$$

and $$-CR^8=CR^8-CR^8=N- \quad (b\text{-}5);$$

wherein $R^8$ is defined as above;
$R^3$ is selected from the group consisting of hydrogen, halo, hydroxy, alkyl, oxo, alkyloxy, Ar, Ar-alkyl, di(Ar—)alkyl, Het and Het-alkyl;
$R^4$ is selected from the group consisting of hydrogen, alkyl, amino, alkylamino, Ar-amino, Het-amino, Het-alkylamino, alkylcarbonylamino, Ar-carbonylamino, Het-carbonylamino, alkylaminocarbonylamino, Ar-aminocarbonylamino, Het-aminocarbonylamino, alkyloxyalkylamino, Ar-oxyalkylamino or Het-oxyalkylamino;
$R^5$ is hydrogen and alkyl;
or $R^4$ and $R^5$ together may form a radical of Formula $$-M-CR^9=CR^{10}- \quad (c\text{-}1);$$

$$-CR^{10}=CR^9-M- \quad (c\text{-}2);$$

$$-M-CR^8R^8-CR^8R^8- \quad (c\text{-}3);$$

$$-CR^8R^8-CR^8R^8-M- \quad (c\text{-}4);$$

$$-CR^8=N-NR^7- \quad (c\text{-}5);$$

$$-NR^7-N=CR^8- \quad (c\text{-}6);$$

$$-CR^9=CR^{10}-CR^9=CR^{10}- \quad (c\text{-}7);$$

$$-CR^8R^8-CR^8R^8-CR^8R^8-M- \quad (c\text{-}8);$$

$$-M-CR^8R^8-CR^8R^8-CR^8R^8- \quad (c\text{-}9);$$

$$-CR^8R^8-CR^8=N-NR^7- \quad (c\text{-}10);$$

$$-NR^7-N=CR^8-CR^8R^8- \quad (c\text{-}11);$$

$$=N-CR^9=CR^{10}- \quad (c\text{-}12);$$

or $$-CR^9=CR^{10}-N= \quad (c\text{-}13);$$

wherein:
$R^7$ and $R^8$ are defined as above;
$R^9$, $R^{10}$ independently are selected from the group consisting of hydrogen, alkyl, halo and haloalkyl; or $R^9$ and $R^{10}$ together may form a bivalent radical of formula —$CR^8=CR^8-CR^8=CR^8$— wherein $R^8$ is defined as above; and
M is selected from the group consisting of a bivalent radical of formula —$CH_2$—, —O—, —S— and —$NR^7$— wherein $R^7$ is defined as above;
Ar is a homocycle selected from the group consisting of naphthyl and phenyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl and mono- or dialkylaminocarbonyl;
Het is a monocyclic heterocycle selected from the group consisting of pyrrolyl, pyrazolyl, imidazolyl, furyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuryl, isoindolyl and benzothienyl; each monocyclic and bicyclic heterocycle may optionally be substituted on a carbon atom with one or more halo, oxo, hydroxy, alkyl and alkyloxy radicals;
alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with one or more halo, hydroxy, alkyloxy or oxo radicals;
halo is a substituent selected from the group consisting of fluoro, chloro, bromo and iodo; and
haloalkyl is a straight or branched saturated hydrocarbon radical having from 1 to 6 carbon atoms or a cyclic saturated hydrocarbon radical having from 3 to 6 carbon atoms, wherein one or more carbonatoms are substituted with one or more halo-atoms.

2. A compound according to claim 1, wherein Ar is naphthyl or phenyl, each radical optionally substituted with 1 or 2 substituents, each substituent independently selected from the group of halo or alkyl; Het is pyridinyl, pyrazinyl, indolyl or isoindolyl, each radical optionally substituted on carbon atom with one or more oxo or alkyl radicals; alkyl is methyl, ethyl, n-propyl, n-butyl n-pentyl or cyclohexylmethyl; halo is fluoro or chloro and haloalkyl is trifluoromethyl.

3. A compound according to claim 1, wherein -A-B— is a bivalent radical of formula (a-2) or (a-3), wherein E is a bivalent radical of formula —S— or —NR$^7$ -wherein R$^7$ is alkyl and wherein R$^8$ is hydrogen and —C-D- is a bivalent radical of formula (b-1) or (b-2) wherein R$^8$ is hydrogen.

4. A compound according to claim 1, wherein R$^1$ and R$^2$, each independently, are selected from the group consisting of hydrogen, alkyl, Ar, Ar-alkyl, Het and Het-alkyl.

5. A compound according to claim 1, where X is a bivalent radical of formula —CH$_2$—, —CH$_2$CH$_2$—, —CH$_2$CH$_2$CH$_2$—, —CH$_2$CH$_2$CH$_2$CH$_2$— or, —CH$_2$CH$_2$CH$_2$CH$_2$CH$_2$— wherein one or more —CH$_2$— groups may be optionally replaced with —CO— or —NR$^7$— wherein R$^7$ is alkylcarbonyl.

6. A compound according to claim 1, wherein R$^3$ is selected from the group consisting of alkyl and oxo, Z is —NR$^7$ in which case; a is a single bond and R$^7$ is Selected from the group consisting of alkyl, pyridinylalkyl, phenylalkyl and Pyrazinylalkyl.

7. A compound according to claim 6 characterized in that R$^9$ and R$^{10}$ together form a radical of formula- —CR$^8$=CR$^8$—CR$^8$=CR$^8$— wherein R$^8$ is hydrogen.

8. A compound according to Formula (I),

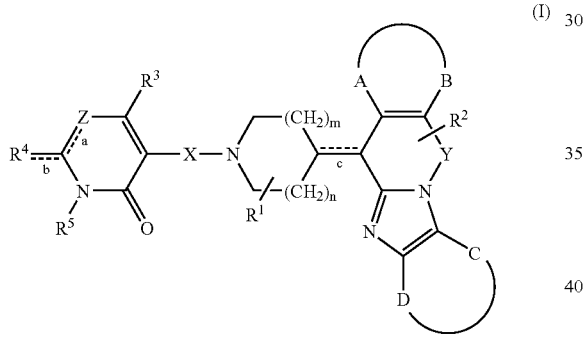

(I)

the pharmaceutically acceptable acid or base addition salts thereof, the sterochemically isomeric forms thereof and the N-oxide form thereof, wherein:
  m is 1;
  n is 1;
  a, b, c independently are a single or a double bond;
  X is a bivalent C$_{1-5}$alkanediyl radical wherein one or more —CH$_2$— groups may be optionally replaced with —CO—, or —NR$^{7a}$; wherein R$^{7a}$ is alkylcarbonyl
  Y is —CH$_2$—CH$_2$—;
  Z is N, in which case a is a double bond and b is a single bond, or is —NR$^{7b}$ in which case a is a single bond and R$^{7b}$ is selected from the group consisting of alkyl, pyridinylalkyl, phenylalkyl and pyrazinylalkyl;
  R$^1$, R$^2$ independently are selected from the group consisting of hydrogen, alkyl, benzyl, naphthylmethyl, isoindolyl and phenyl;
  -A-B— independently is selected from the group consisting of bivalent radical of formula —CH=CH-E-   (a-2);

and

—CH=CH—CH=CH—   (a-3);

E is a bivalent radical of formula —S— or —NR$^{7c}$— wherein R$^{7c}$ is alkyl;
  —C-D- independently is selected from the group consisting of bivalent radical of formula —CH=CH—CH=CH—   (b1);

and

—N=CH—CH=CH—   (b-2);

R$^3$ is alkyl or oxo;
  R$^4$ is selected from the group consisting of amino, alkylamino, pyridinylalkylamino, phenylcarbonylamino, alkylanrinocarbonylamino and alkyloxyalkylamino;
  R$^5$ is alkyl;
  or R$^4$ and R$^5$ together may form a radical of Formula -M-CR$^9$=CR$^{10}$—   (c-1);

—CR$^{10}$=CR$^9$-M-   (c-2);

-M-CR$^8$R$^8$—CR$^8$R$^8$—   (c-3);

—NR$^{7d}$—N=CR$^8$—   (c-6);

—CR$^9$=CR$^{10}$—CR$^9$=CR$^{10}$—   (c-7);

-M-CR$^8$R$^8$—CR$^8$R$^8$—CR$^8$R$^8$—   (c-9);

—NR$^{7d}$—N=CR$^8$—CR$^8$R$^8$—   (c-11);

or

=N—CR$^9$=CR$^{10}$—   (c-12);

wherein
  R$^7$ is selected from the group consisting of alkyl, benzyl, pyridinylalkyl, alkyloxyalkyl, pyrazinylalkyl, alkyloxyalkyloxyalkyl, mono- or dialkylaminoalkyl, alkyloxycarbonylalkyl, hydroxyalkyl, isoindol-1,3-dionyl, aminocarbonylalkyl, hydroxyalkyloxyalkyl, alkylcarbonyloxyalkyloxyalkyl; aminoalkyl, alkylcarbonylaminoalkyl and alkyloxyalkyl; R$^8$ is hydrogen, alkyl, halo and haloalkyl;
  R$^9$, R$^{10}$ independently are selected from the group consisting of hydrogen, alkyl, halo and haloalkyl; or R$^9$ and R$^{10}$ together may form a radical of formula —CH=CH—CH=CH— and M is a bivalent radical of formula —O—, —S— or —NR$^{7e}$—, wherein R$^{7e}$ is alkyl.

9. A compound according to claim 1, wherein the compound is 3-[2-[4-(11,12-dihydro-6H-benzimidazo[2,1-b][3]benzazepin-6-yl)-2-(phenylmethyl)-1-piperidinyl]ethyl]-2,10-dimethyl pyrimido [1,2-α]benzimidazol-4(10H)-one, the pharmaceutically acceptable acid or base addition salts thereof, the stereochemically isomeric forms thereof and the N-oxide form thereof.

10. An acid addition salt according to claim 9, wherein the compound is 3-[2-[4-(11,12-dihydro-6H-benzimidazo[2,1-b][3]benzazepin-6-yl)-2-(phenylmethyl)-1-piperidinyl]ethyl]-2,10-dimethyl pyrimido [1,2-α]benzimidazol-4(10H)-one (E)-2-butenedioate (2:3) hydrate (1:1) and stereoisomeric forms thereof.

11. A compound according to claim 9, wherein the compound is the (A)[(2α, 4β)(A)] enantiomer, the (B)[(2α, 4β)(A)] enantiomer or a mixture thereof.

12. A compound which is degraded in vivo to yield a compound according to claim 10.

13. A composition comprising a pharmaceutically acceptable carrier and, as active ingredient, a therapeutically effective amount of a compound as defined in claim 1.

14. A composition according to claim 13, formulated as an injectable or perfusable solution or suspension.

15. A process for preparing a compound Formula I,

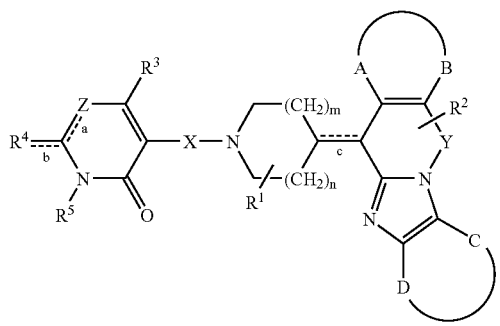

the pharmaceutically acceptable acid or base addition salts thereof, the stereochemically isomeric forms thereof and the N-oxide form thereof, wherein:

m is 1;

n is 1;

a, b, c independently are a single or a double bond;

X is a covalent bond or a bivalent $C_{1-6}$alkanediyl radical wherein one or more —$CH_2$— groups may be optionally replaced with —O—, —S—, —C(=O)— or $NR^7$—; wherein:

R$^7$ is selected from the group consisting of hydrogen, alkyl, Ar, Ar-alkyl, Het, Het-alkyl, hydroxyalkyl, alkyloxy, alkyloxyalkyl, alkyloxyalkyloxyalkyl, aminoalkyl, mono- or dialkylaminoalkyl, formyl, alkylcarbonylaminoalkyl, alkylcarbonyloxyalkyl, alkyloxycarbonyl, alkyloxycarbonylalkyl, alkylaminocarbonyl, alkylaminocarbonylalkyl, hydroxyalkyloxyalkyl, aminocarbonyl, aminocarbonylalkyl, alkyloxycarbonyl, alkylcarbonyl and alkylcarbonyloxyalkyloxyalkyl;

Y is —$CH_2$—$CH_2$—;

Z is N, in which case a is a double bond and b is a single bond; or is N—$R^7$ in which case a is a single bond and $R^7$ is defined as above;

$R^1$, $R^2$ independently are selected from the group consisting of hydrogen, hydroxy, alkyl, alkyloxy, Ar, Ar-alkyl, di(Ar—)alkyl, Het and Het-alkyl;

-A-B— independently is selected from the group consisting of a bivalent radical of formula -E-CR$^8$=CR$^8$— (a-1);

—CR$^8$=CR$^8$-E- (a-2);

and

—CR$^8$=CR$^8$—CR$^8$=CR$^8$— (a-3);

wherein:

R$^8$ each independently is selected from the group consisting of hydrogen, halo, hydroxy, alkyl or alkyloxy;

E is selected from the group consisting of a bivalent radical of formula —O—, —S— and —NR$^7$— wherein R$^7$ is defined as above;

—C-D- independently is selected from the group consisting of a bivalent radical of formula —CR$^8$=CR$^8$—CR$^8$=CR$^8$— (b-1);

—N=CR$^8$—CR$^8$=CR$^8$— (b-2);

—CR$^8$=N—CR$^8$=CR$^8$— (b-3);

—CR$^8$=CR$^8$—N=CR$^8$— (b-4);

and

—CR$^8$=CR$^8$—CR$^8$=N— (b-5);

wherein R$^8$ is defined as above;

R$^3$ is selected from the group consisting of hydrogen, halo, hydroxy, alkyl, oxo, alkyloxy, Ar, Ar-alkyl, di(Ar—)alkyl, Het and Het-alkyl;

R$^4$ is selected from the group consisting of hydrogen, alkyl, amino, alkylamino, Ar-amino, Het-amino, Het-alkylamino, alkylcarbonylamino, Ar-carbonylamino, Het-carbonylamino, alkylaminocarbonylamino, Ar-aminocarbonylamino, Het-aminocarbonylamino, alkyloxyalkylamino, Ar-oxyalkylamino or Het-oxyalkylamino;

R$^5$ is hydrogen and alkyl;

or R$^4$ R$^5$ together may form a radical of Formula

-M-CR$^9$=CR$^{10}$— (c-1);

—CR$^{10}$=CR$^9$-M- (c-2);

-M-CR$^8$R$^8$—CR$^8$R$^8$— (c-3);

—CR$^8$R$^8$—CR$^8$R$^8$-M- (c-4);

—CR$^8$=N—NR$^7$— (c-5);

—NR$^7$—N=CR$^8$— (c-6);

—CR$^9$=CR$^{10}$—CR$^9$=CR$^{10}$— (c-7);

—CR$^8$R$^8$—CR$^8$R$^8$—CR$^8$R$^8$-M- (c-8);

-M-CR$^8$R$^8$—CR$^8$R$^8$—CR$^8$R$^8$— (c-9);

—CR$^8$R$^8$—CR$^8$=N—NR$^7$— (c-10);

—NR$^7$—N=CR$^8$—CR$^8$R$^8$— (c-11);

=N—CR$^9$=CR$^{10}$— (c-12);

or

—CR$^9$=CR$^{10}$—N= (c-13);

wherein:

R$^7$ and R$^8$ are defined as above;

R$^9$, R$^{10}$ independently are selected from the group consisting of hydrogen, alkyl, halo and haloalkyl; or R$^9$ and R$^{10}$ together may form a bivalent radical of formula —CR$^8$=CR$^8$—CR$^8$=CR$^8$— wherein R$^8$ is defined as above; and M is selected from the group consisting of a bivalent radical of formula —$CH_2$—, —O—, —S— and —NR$^7$— wherein R$^7$ is defined as above;

Ar is a homocycle selected from the group consisting of naphthyl and phenyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl and mono- or dialkylaminocarbonyl;

Het is a monocyclic heterocycle selected from the group consisting of pyrrolyl, pyrazolyl, imidazolyl, furyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuryl, isoindolyl and benzothienyl ; each monocyclic and bicyclic heterocycle may optionally be substituted on a carbon atom with one or more halo, oxo, hydroxy, alkyl and alkyloxy radicals;

alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with one or more halo, hydroxy, alkyloxy or oxo radicals;

halo is a substituent selected from the group consisting of fluoro, chloro, bromo and iodo; and haloalkyl is a straight or branched saturated hydrocarbon radical having from 1 to 6 carbon atoms or a cyclic saturated hydrocarbon radical having from 3 to 6 carbon atoms, wherein one or more carbonatoms are substituted with one or more halo-atoms;

wherein a compound of Formula (II) is reacted with a compound of Formula (III) according to the following reaction:

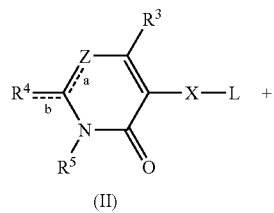

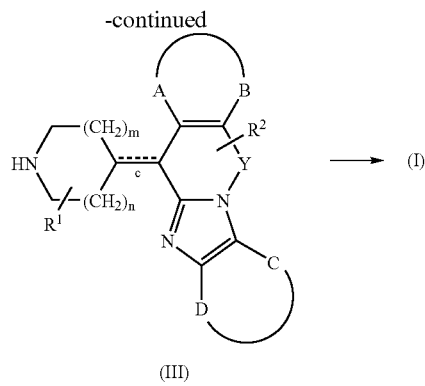

wherein all variables are defined as in Formula (I) and L represents any suitable reactive leaving group.

16. Method for the treatment of elevated intracranial pressure and/or secondary ischaemia comprising administering to a patient in need of treatment the compound of claim 1.

17. Method for the treatment for the reduction of intracranial pressure (ICP)-comprising administering to a patient who has been identified as at risk of developing ICP or is in need of treatment for ICP the compound of claim 1.

18. The process of claim 15 wherein the leaving groups selected from the group consisting of halo and sulfonyloxy.

19. A compound according to claim 1, wherein $R^4$ and $R^5$ together form a bivalent radical selected from the group consisting of Formula (c-1), (c-2), (c-3), (c-6), (c-7), (c-9), (c-11) and (c-12) wherein $R^7$ is selected from the group consisting of alkyl, benzyl, pyridinylalkyl, alkyloxyalkyl, pyrazinylalkyl, alkyloxyalkyloxyalkyl, mono- or dialkylaminoalkyl, alkyloxycarbonylalkyl, hydroxyalkyl, isoindol- 1,3-dionyl, aminocarbonylalkyl, hydroxyalkyloxyalkyl, alkylcarbonyloxyalkyloxyalkyl; aminoalkyl, alkylcarbonylaminoalkyl and alkyloxyalkyl; and $R^8$ is selected from the group consisting of hydrogen, alkyl, halo and haloalkyl.

* * * * *